US012734223B2

(12) United States Patent
Gross et al.

(10) Patent No.: US 12,734,223 B2

(45) Date of Patent: Sep. 15, 2026

(54) BROMELAIN PROTEASE, BROMELAIN, JACALIN-LIKE LECTIN, EXTRACT FROM THE STEM AND/OR THE FRUIT OF A PINEAPPLE PLANT, COMBINATION PREPARATION, BROMELAIN PROTEASE INHIBITOR, PROTEIN/PROTEASE MIX, AND GLYCATED BROMELAIN PROTEIN FORMED BY EXOGENOUS NON-ENZYMATIC GLYCATION, FOR USE IN THE TREATMENT OR PROPHYLAXIS OF VIRUS INFECTIONS CAUSED BY CORONAVIRUSES IN A HUMAN OR ANIMAL

(71) Applicants: URSAPHARM ARZNEIMITTEL GMBH, Saarbrücken (DE); HOCHSCHULE KAISERSLAUTERN, Pirmasens (DE); HELMHOLTZ-INSTITUT FÜR PHARMAZEUTISCHE FORSCHUNG SAARLAND, Saarbrücken (DE)

(72) Inventors: Peter Gross, Pirmasens (DE); Rolf Müller, Saarbrücken (DE); Frank Holzer, Saarbrücken (DE); Peter Meiser, Saarbrücken (DE); Holger Seelert, Pirmasens (DE)

(73) Assignees: Ursapharm Arzneimittel GmbH, Saarbrücken (DE); Hochschule Kaiserslautern, Pirmasens (DE); Helmholtz-Institut für Pharmazeutische Forschung Saarland, Saarbrücken (DE)

(*) Notice: Subject to any disclaimer, the term of this patent is extended or adjusted under 35 U.S.C. 154(b) by 634 days.

(21) Appl. No.: 18/000,984

(22) PCT Filed: Jun. 10, 2021

(86) PCT No.: PCT/EP2021/065709

§ 371 (c)(1),
(2) Date: Dec. 7, 2022

(87) PCT Pub. No.: WO2021/250207

PCT Pub. Date: Dec. 16, 2021

(65) Prior Publication Data

US 2024/0216484 A1 Jul. 4, 2024

(30) Foreign Application Priority Data

Jun. 10, 2020 (DE) ..................... 10 2020 004 632.0
Jun. 10, 2020 (DE) ..................... 10 2020 004 633.9
(Continued)

(51) Int. Cl.
*A61K 38/48* (2006.01)
*A61K 31/685* (2006.01)
(Continued)

(52) U.S. Cl.
CPC ........ *A61K 38/4873* (2013.01); *A61K 31/685* (2013.01); *A61K 36/88* (2013.01);
(Continued)

(58) Field of Classification Search
None
See application file for complete search history.

(56) References Cited

U.S. PATENT DOCUMENTS

2007/0160696 A1* 7/2007 Clymer .................. A61K 36/19
424/773

FOREIGN PATENT DOCUMENTS

WO WO 01/87229 * 11/2001
WO WO 2015/116375 A1 8/2015

OTHER PUBLICATIONS

Gross et al., J. Phar. Biomed. Anal. 181: 113075 (published Jan. 8, 2020).*

(Continued)

*Primary Examiner* — Erin M. Bowers

(74) *Attorney, Agent, or Firm* — Leydig, Voit & Mayer, Ltd.

(57) ABSTRACT

The present invention addresses the problem of indicating active-ingredient classes which can treat virus diseases
(Continued)

Sequence (from N to the C terminus M (mean)

| SEQ ID No. | Name | Sequence (from N- to C-terminal) | M (mono) [Da] | M (middle) [Da] |
|---|---|---|---|---|
| 1 | I | HC: EYKCYCTDTYSDCPGFCKKCKAEFGKYICLDLISPNDCVK LC: ACSECVCPLR | 5644.5 | 5648.6 |
| 2 | II | HC: EEYKCYCTDTYSDCPGFCKKCKAEFGKYICLDLISPNDCVK LC: ACSECVCPLR | 5773.5 | 5777.7 |
| 3 | III | HC: EEYKCYCTDTYSDCPGFCKKCKAEFGKYICLDLISPNDCVK LC: TACSECVCPLR | 5874.5 | 5878.5 |
| 4 | IV | HC: EEYKCYCTDTYSDCPGFCKTCKAEFGKYICLDLISPNDCVK LC: ACSECVCPLR | 5746.5 | 5750.6 |
| 5 | V | HC: EEYKCYCTDTYSDCPGFCKTCKAEFGKYICLDLISPNDCVK LC: TACSECVCPLR | 5847.5 | 5851.7 |
| 6 | VI | HC: DEYKCYCADTYSDCPGFCKKCKAEFGKYICLDLISPNDCVK LC: TACSECVCPLQ | 5802.5 | 5806.7 |
| 7 | VII | HC: DEYKCYCADTYSDCPGFCKKCKAEFGKYICLDLISPNDCVK LC: TACSECVCPL | 5674.4 | 5678.6 |

caused by coronaviruses in a human or animal. Said treatment includes the acute treatment of an already existing virus disease and the prophylaxis of same. The present invention relates to a bromelain protease, bromelain, jacalin-like lectin, extract from the stem and/or the fruit of a pineapple plant, combination preparation, bromelain protease inhibitor, protein/protease mix, and glycated bromelain protein formed by exogenous non-enzymatic glycation, for use in the treatment or prophylaxis of virus infections caused by coronaviruses in a human or animal.

7 Claims, 22 Drawing Sheets

Specification includes a Sequence Listing.

(30) Foreign Application Priority Data

Jun. 10, 2020 (DE) ..................... 10 2020 004 634.7
Jun. 10, 2020 (DE) ..................... 10 2020 004 635.5
Jun. 10, 2020 (DE) ..................... 10 2020 207 281.7

(51) Int. Cl.
*A61K 36/88* (2006.01)
*A61P 31/14* (2006.01)
*C12N 9/50* (2006.01)

(52) U.S. Cl.
CPC ................ *A61P 31/14* (2018.01); *C12N 9/63* (2013.01); *C12Y 304/22031* (2013.01); *C12Y 304/22032* (2013.01); *C12Y 304/22033* (2013.01)

(56) References Cited

OTHER PUBLICATIONS

Shi, "Authoritative release: Bromelain, phentolamine, and anisodamine are expected to prevent and treat severe new coronavirus pneumonia," Feb. 2020.*

Hatano et al., "Primary Structure, Sequence-Specific 1H-NMR Assignments and Secondary Structure in Solution of Bromelain Inhibitor VI from Pineapple Stem," *Eur. J. Biochem* 232(2): 334-343 (1995).

Hatano et al., "The Amino Acid Sequences of Isoforms of the Bromelain Inhibitor from Pineapple Stem," *J. Biochem* 124(2): 457-461 (1998).

Lenarčič et al., "Characterization and Structure of Pineapple Stem Inhibitor of Cysteine Proteinases," *Biol. Chem. Hoppe-Seyler* 373: 459-464 (1992).

Owoyele et al., "Bromelain: A Review on its Potential as a Therapy for the Management of Covid-19," *Nigerian Journal of Physiological Sciences*, 35(1): 10-19 (2020)—(downloaded Jan. 27, 2023) https://ojshostng.com/index.php/niphysiologicalsciences/article/view/573.

Reddy et al., "Primary structural analysis of sulfhydryl protease inhibitors from pineapple stem," *J. Biol. Chem* 250(5): 1741-1750 (1975).

Ziółkowska et al., "Domain-swapped structure of the potent antiviral protein griffithsin and its mode of carbohydrate binding," *Structure* 14(7): 1127-1135 (2006).

European Patent Office, International Search Report in International Application No. PCT/EP2021/065709 (Oct. 1, 2021).

European Patent Office, Written Opinion in International Application No. PCT/EP2021/065709 (Oct. 1, 2021).

International Bureau of WIPO, International Preliminary Report on Patentability in International Application No. PCT/EP2021/065709 (Dec. 13, 2022).

Gross et al., "Characterization of bromelain indicates a molar excess of inhibitor vs. enzyme molecules, a Jacalin-like lectin and Maillard reaction products," *J Phar Biomed Anal* 181: 113075 (2020).

Harrach et al., "Isolation and Partial Characterization of Basic Proteinases from Stem Bromelain," *J Protein Chem* 14(1): 41-52 (1995).

Hatano et al., "Solution Structure of Bromelain Inhibitor IV from Pineapple Stem: Structural Similarity with Bowman-Birk Trypsin/Chymotrypsin Inhibitor from Soybean," *Biochemistry* 35(17): 5379-5384 (1996).

Hatano et al., "Structure-Function Relationship of Bromelain Isoinhibitors from Pineapple Stem," *Biol. Chem.* 383(7-8): 1151-1156 (2002).

Perlstein et al., "Isolation and characterization of a protease inhibitor from commercial stem bromelain acetone powder," *J Supramol Struct* 1(3): 249-254 (1973).

Rowan et al., "Ananain: A novel cysteine proteinase found in pineapple stem," *Archives of Biochemistry and Biophysics* 267(1): 262-270 (1988).

Azarkan et al., "Biochemical and structural characterization of a mannose binding jacalin related lectin with two sugar binding sites from pineapple (Ananas comosus) stem," *Scientific Reports* 8:11508 (2018) 14 pgs.

Islam et al., "Natural products and their derivatives against coronavirus: A review of the non clinical and pre-clinical data," *Phytotherapy Research* (2020), pp. 1-22.

权威发布：菠萝 蛋白酶、酚妥拉明 和山莨菪碱有望 防治重症新型冠状 病毒肺炎 ("Authoritative release: Bromelain, phentolamine and anisodamine are expected to prevent and treat severe new coronavirus pneumonia"), Shi Zhonghui, Editor (Feb. 2020) https://mp.weixin.gg.com/s?__biz=MzU2MikzNDA5Ng==&mid=2247484435&idx=2&sn=da08138717ed0f531d73ef6fdffad360&chksm=fc60bc2ccb17353a8b54a6016fe7c613b3107f68ef20c50b3839c8803eab36ce7e4a240f0cd3&scene=27.

China National Intellectual Property Administration, Second Office Action in Chinese Patent Application No. 202180056115.0 (May 20, 2025).

* cited by examiner

Figure 1

Sequence (from N to the C terminus M (mean)

| SEQ ID No. | Name | Sequence (from N- to C-terminal) | M (mono$_i$) [Da] | M (middle) [Da] |
|---|---|---|---|---|
| 1 | I | HC: EYKCYCTDTYSDCPGFCKKCKAEFGKYICLDLISPNDCVK<br>LC: ACSECVCPLR | 5644.5 | 5648.6 |
| 2 | II | HC: EEYKCYCTDTYSDCPGFCKKCKAEFGKYICLDLISPNDCVK<br>LC: ACSECVCPLR | 5773.5 | 5777.7 |
| 3 | III | HC: EEYKCYCTDTYSDCPGFCKKCKAEFGKYICLDLISPNDCVK<br>LC: TACSECVCPLR | 5874.5 | 5878.8 |
| 4 | IV | HC: EEYKCYCTDTYSDCPGFCKTCKAEFGKYICLDLISPNDCVK<br>LC: ACSECVCPLR | 5746.5 | 5750.6 |
| 5 | V | HC: EEYKCYCTDTYSDCPGFCKTCKAEFGKYICLDLISPNDCVK<br>LC: TACSECVCPLR | 5847.5 | 5851.7 |
| 6 | VI | HC: DEYKCYCADTYSDCPGFCKKCKAEFGKYICLDLISPNDCVK<br>LC: TACSECVCPLQ | 5802.5 | 5806.7 |
| 7 | VII | HC: DEYKCYCADTYSDCPGFCKKCKAEFGKYICLDLISPNDCVK<br>LC: TACSECVCPL | 5674.4 | 5678.6 |

Fig. 4

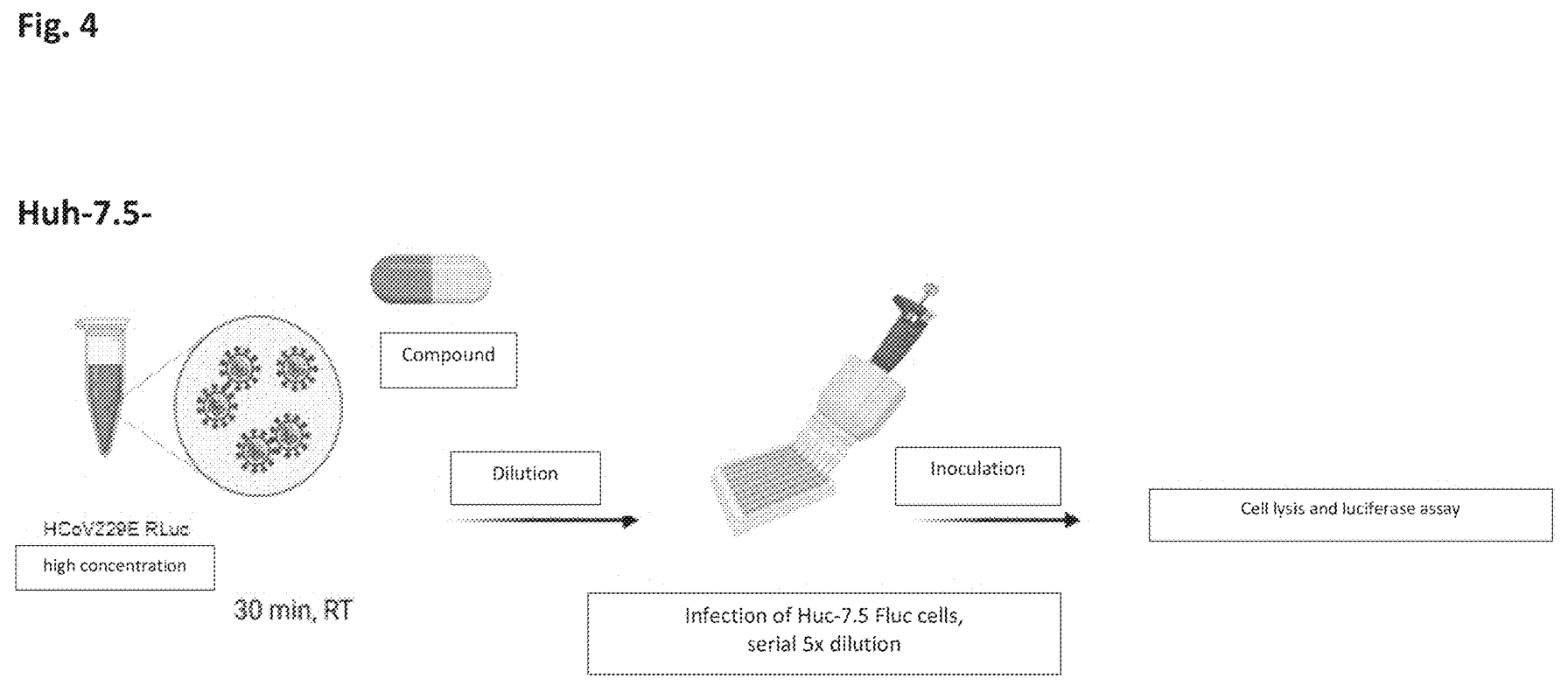

Huh-7.5-

HCoV229E RLuc high concentration 30 min, RT

Compound

Dilution

Inoculation

Infection of Huc-7.5 Fluc cells,
serial 5x dilution

Cell lysis and luciferase assay

% of the TBS control

Fig. 7
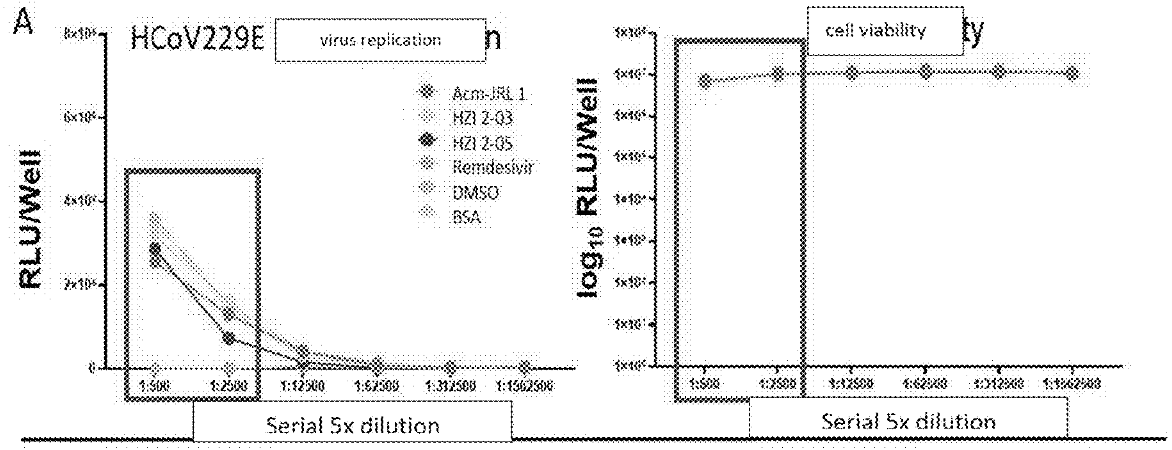
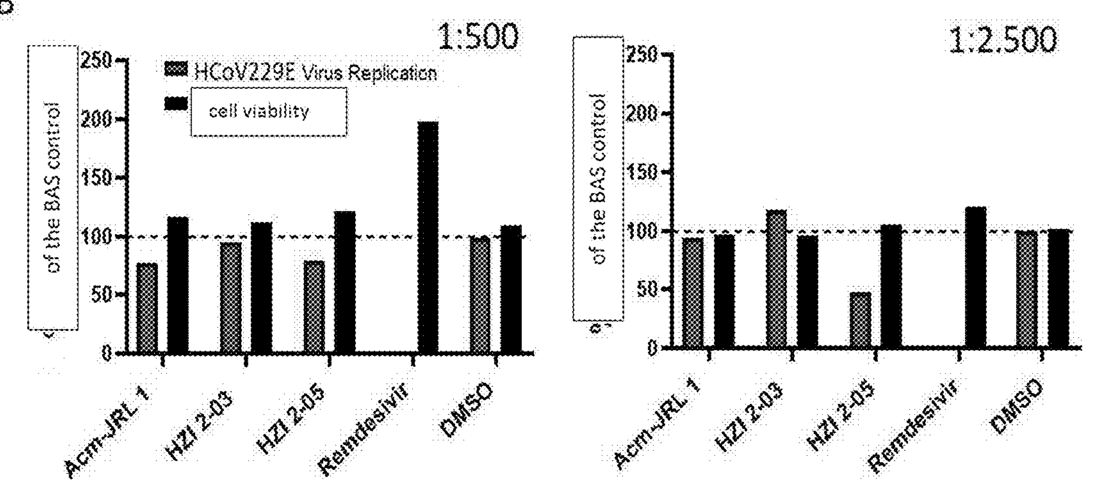

Antec HZI2-05
Antec HZI2-05_final
Antec HZI2-05_final_2ndDer
AU
1.5
1.0
0.5
0.0
Wavelength in nm
250
300
350
400
280.0
253.0
258.9
265.9
271.8
276.8
282.8
291.7
297.6

A
B
C
D
E
RU
Response
Time

Fig. 15

~180 kDa
~130 kDa
~100 kDa
~70 kDa
~55 kDa
~40 kDa
~35 kDa
~25 kDa
~15 kDa
~10 kDa

| | 1 | 2 | 3 | 4 | 5 | 6 | 7 | 8 | 9 | 10 |
|---|---|---|---|---|---|---|---|---|---|---|
| Spike, ratio | | 1 | 1 | 1 | 1 | 1 | 1 | 1 | 1 | 1 |
| Protease, ratio | | 1 | 1 | 1 | 1 | 1 | 1 | 1 | 1 | 1 |
| Inhibitor, ratio | | | | | | | | 1 | 1 | 1 |
| Incubation time, min | | 10 | 20 | 30 | 60 | 90 | 120 | 10 | 20 | 30 |
| temperature, °C | | 37 | 37 | 37 | 37 | 37 | 37 | 37 | 37 | 37 |

1
2
3
4
5
6
7
~180 kDa
~130 kDa
~100 kDa
~70 kDa
~55 kDa
~40 kDa
~35 kDa
~25 kDa
~15 kDa
~10 kDa
Spike, ratio 10 100 1 10 100 1
Protease, ratio 1 1 1 1 1 1
Inhibitor, ratio 0,5 0,5
Incubation time, min 10 10 10 120 120 120
temperature °C 37 37 37 37 37 37

Fig. 18 s_to_p_100_to_1_10min_RCS_1_10852.d: TIC +All MS

Figure 18:
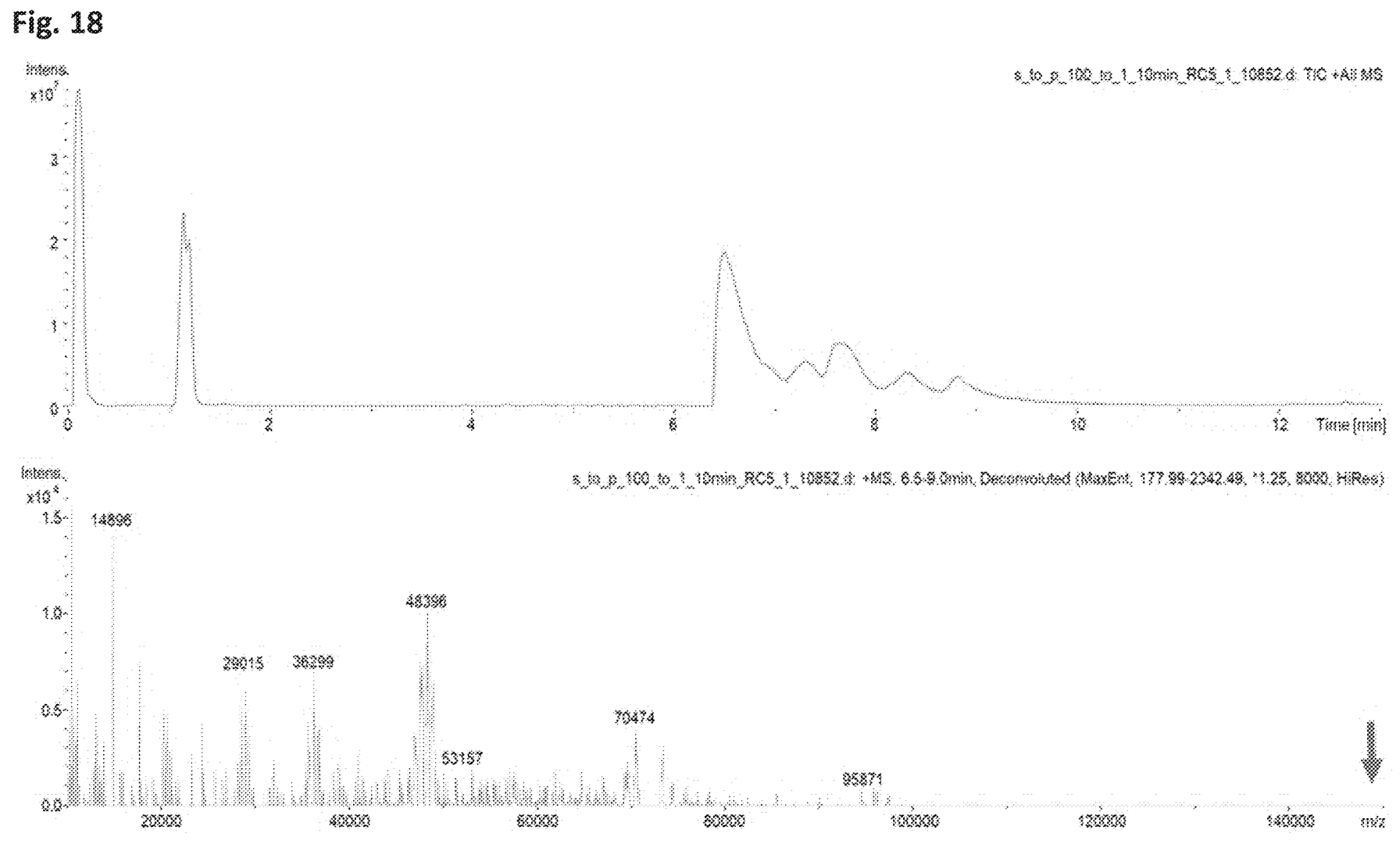

Intens. x10^7

Time [min]

s_to_p_100_to_1_10min_RCS_1_10852.d: +MS, 6.6-9.0min, Deconvoluted (MaxEnt, 177.99-2342.49, *1.25, 8000, HiRes)

Intens. x10^4

14896

29015

36299

48396

53157

70474

95871 m/z

Intens.
x10^7
s_to_p_100_to_1_2h_RC7_1_10854.d: TIC +All MS
Time [min]
Intens.
x10^4
s_to_p_100_to_1_2h_RC7_1_10854.d: +MS, 6.5-9.0min, Deconvoluted (MaxEnt, 177.99-2345.44, *1.25, 8000, HiRes)
14896
24392
29038
36297
48398
58567
70505
85482
95873
m/z spike_prot_120min_BD3_1_10435.d: TIC +All MS
Intens. x10^7
Time [min]
spike_prot_120min_BD3_1_10435.d: +MS, 6.5-9.0min, Deconvoluted (MaxEnt, 177.99-2236.71, *1.25, 8000, HiRes)
Intens. x10^4
24392
37180
47647
72537
m/z

Fig 21 kDa
~ 245
~ 75
~ 48
~ 35
~ 25
~ 20
~ 17
~ 11
~ 5
10
9
8
7
6
5
4
3
2

SEQUENCE LISTING

```
<160> NUMBER OF SEQ ID NOS: 7

<210> SEQ ID NO 1
<211> LENGTH: 50
<212> TYPE: PRT
<213> ORGANISM: Artificial Sequence
<220> FEATURE:
<223> OTHER INFORMATION: Bromelain-Proteaseinhibitor I

<400> SEQUENCE: 1

Glu Tyr Lys Cys Tyr Cys Thr Asp Thr Tyr Ser Asp Cys Pro Gly Phe
1               5                   10                  15

Cys Lys Lys Cys Lys Ala Glu Phe Gly Lys Tyr Ile Cys Leu Asp Leu
            20                  25                  30

Ile Ser Pro Met Asp Cys Val Lys Ala Cys Ser Glu Cys Val Cys Pro
        35                  40                  45

Leu Arg
    50


<210> SEQ ID NO 2
<211> LENGTH: 51
<212> TYPE: PRT
<213> ORGANISM: Artificial Sequence
<220> FEATURE:
<223> OTHER INFORMATION: Bromelain-Proteaseinhibitor II

<400> SEQUENCE: 2

Glu Glu Tyr Lys Cys Tyr Cys Thr Asp Thr Tyr Ser Asp Cys Pro Gly
1               5                   10                  15

Phe Cys Lys Lys Cys Lys Ala Glu Phe Gly Lys Tyr Ile Cys Leu Asp
            20                  25                  30

Leu Ile Ser Pro Asn Asp Cys Val Lys Ala Cys Ser Glu Cys Val Cys
        35                  40                  45

Pro Leu Arg
    50
```

```
<210> SEQ ID NO 3
<211> LENGTH: 52
<212> TYPE: PRT
<213> ORGANISM: Artificial Sequence
<220> FEATURE:
<223> OTHER INFORMATION: Bromelain-Proteaseinhibitor III

<400> SEQUENCE: 3

Glu Glu Tyr Lys Cys Tyr Cys Thr Asp Thr Tyr Ser Asp Cys Pro Gly
1               5                   10                  15

Phe Cys Lys Lys Cys Lys Ala Glu Phe Gly Lys Tyr Ile Cys Leu Asp
            20                  25                  30

Leu Ile Ser Pro Asn Asp Cys Val Lys Thr Ala Cys Ser Glu Cys Val
        35                  40                  45

Cys Pro Leu Arg
    50


<210> SEQ ID NO 4
<211> LENGTH: 51
<212> TYPE: PRT
<213> ORGANISM: Artificial Sequence
<220> FEATURE:
<223> OTHER INFORMATION: Bromelain-Proteaseinhibitor IV

<400> SEQUENCE: 4

Glu Glu Tyr Lys Cys Tyr Cys Thr Asp Thr Tyr Ser Asp Cys Pro Gly
1               5                   10                  15

Phe Cys Lys Thr Cys Lys Ala Glu Phe Gly Lys Tyr Ile Cys Leu Asp
            20                  25                  30

Leu Ile Ser Pro Asn Asp Cys Val Lys Ala Cys Ser Glu Cys Val Cys
        35                  40                  45

Pro Leu Arg
    50


<210> SEQ ID NO 5
<211> LENGTH: 52
<212> TYPE: PRT
<213> ORGANISM: Artificial Sequence
<220> FEATURE:
<223> OTHER INFORMATION: Bromelain-Proteaseinhibitor V

<400> SEQUENCE: 5

Glu Glu Tyr Lys Cys Tyr Cys Thr Asp Thr Tyr Ser Asp Cys Pro Gly
1               5                   10                  15

Phe Cys Lys Thr Cys Lys Ala Glu Phe Gly Lys Tyr Ile Cys Leu Asp
            20                  25                  30

Leu Ile Ser Pro Asn Asp Cys Val Lys Thr Ala Cys Ser Glu Cys Val
        35                  40                  45

Cys Pro Leu Arg
    50


<210> SEQ ID NO 6
<211> LENGTH: 52
<212> TYPE: PRT
<213> ORGANISM: Artificial Sequence
<220> FEATURE:
<223> OTHER INFORMATION: Bromelain-Proteaseinhibitor VI

<400> SEQUENCE: 6

Asp Glu Tyr Lys Cys Tyr Cys Ala Asp Thr Tyr Ser Asp Cys Pro Gly
1               5                   10                  15
```

```
Phe Cys Lys Lys Cys Lys Ala Glu Phe Gly Lys Tyr Ile Cys Leu Asp
            20                  25                  30

Leu Ile Ser Pro Asn Asp Cys Val Lys Thr Ala Cys Ser Glu Cys Val
        35                  40                  45

Cys Pro Leu Gln
    50


<210> SEQ ID NO 7
<211> LENGTH: 51
<212> TYPE: PRT
<213> ORGANISM: Artificial Sequence
<220> FEATURE:
<223> OTHER INFORMATION: Bromelain-Proteaseinhibitor VII

<400> SEQUENCE: 7

Asp Glu Tyr Lys Cys Tyr Cys Ala Asp Thr Tyr Ser Asp Cys Pro Gly
1               5                   10                  15

Phe Cys Lys Lys Cys Lys Ala Glu Phe Gly Lys Tyr Ile Cys Leu Asp
            20                  25                  30

Leu Ile Ser Pro Asn Asp Cys Val Lys Thr Ala Cys Ser Glu Cys Val
        35                  40                  45

Cys Pro Leu
    50
```

1

BROMELAIN PROTEASE, BROMELAIN, JACALIN-LIKE LECTIN, EXTRACT FROM THE STEM AND/OR THE FRUIT OF A PINEAPPLE PLANT, COMBINATION PREPARATION, BROMELAIN PROTEASE INHIBITOR, PROTEIN/PROTEASE MIX, AND GLYCATED BROMELAIN PROTEIN FORMED BY EXOGENOUS NON-ENZYMATIC GLYCATION, FOR USE IN THE TREATMENT OR PROPHYLAXIS OF VIRUS INFECTIONS CAUSED BY CORONAVIRUSES IN A HUMAN OR ANIMAL

CROSS-REFERENCE TO RELATED APPLICATIONS

This patent application is the U.S. national phase of International Application No. PCT/EP2021/065709, filed on Jun. 10, 2021, which claims the benefit of German Patent Application No. 10 2020 207 281.7, filed Jun. 10, 2020, German Patent Application No. 10 2020 004 632.0, filed Jun. 10, 2020, German Patent Application No. 10 2020 004 633.9, filed Jun. 10, 2020, German Patent Application No. 10 2020 004 634.7, filed Jun. 10, 2020, German Patent Application No. 10 2020 004 635.5, filed Jun. 10, 2020.

INCORPORATION BY REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,963 byte ASCII (Text) file named "7663248_ST25.txt", created on Aug. 8, 2023.

In view of the continuing COVID-19 pandemic there is still an acute need to provide additional active ingredients or active ingredient classes for the treatment of viral diseases.

The present invention therefore has the object of presenting active ingredient classes with which viral diseases caused by coronaviruses in a human or animal can be treated. The treatment in this respect includes the acute treatment of an already present viral disease such as also the prophylaxis thereof.

In accordance with a first aspect, the present invention relates to a bromelain protease (synonym "bromelain") for use in the treatment or prophylaxis of viral infections, caused by coronaviruses, in a human or animal. The bromelain protease is in particular a bromelain protease selected from the group consisting of stem bromelain (SBM) (EC 3.4.22.32, CAS No.: 37189-34-7), fruit bromelain (EC 3.4.22.33, CAS No.: 9001-00-7), ananain (EC 3.4.22.31), and mixtures and combinations thereof.

The manufacture and isolation of bromelain proteases, in particular stem bromelain (SBM) (EC 3.4.22.32) and fruit bromelain (EC 3.4.22.33) from the stem or fruit of pineapple plants (*Ananas comosus*) is known from the prior art and is e.g. described by Rowan, A. D., Buttle, D. J. & Barrett, A. J. in Arch. Biochem. Biophys. 267, 262-270 (1988) or in ARCHIVES OF BIOCHEMISTRY AND BIOPHYSICS, Vol. 267, No. 1, November 15, pp. 262-270 (1988).

In addition to direct antiviral effects, said bromelains also have systemic effects that are helpful overall in the treatment of viral infections. Anti-inflammatory effects that brake an overshooting immune reaction, anti-edematous effects that, for example, counteract edemas in the lung, and anticoagulant effects that counteract thromboses caused by inflammation and/or by an overactive coagulation system can in particular be named here.

In accordance with a second aspect, the present invention relates to a jacalin-related lectin for use in the treatment or prophylaxis of viral infections, caused by coronaviruses, in a human or animal.

Jacalin-related lectin is here in particular selected from the group consisting of mannose-specific and glucose-specific lectins.

Jacalin-related lectin selected from the group consisting of pineapple lectin (jacalin-related lectin from *Ananas comosus* (AcmJRL)), jacalin, artocarpin lectin, MPA lectin, heltuba lectin agglutinin, griffithsin, and mixtures and combinations thereof is particularly preferable.

The invention in a third aspect further relates to an extract from the stem and/or from the fruit of a pineapple plant for use in the treatment or prophylaxis of viral infections, caused by coronaviruses, in a human or animal.

The pineapple plant can in particular be *Ananas comosus* and *Ananas sativus*. Such extracts contain one or more of the previously named bromelain proteases and/or ananain.

In accordance with a fourth aspect, the present invention also relates to a combination preparation containing at least one bromelain protease and at least one jacalin-related lectin for use in the treatment or prophylaxis of viral infections, caused by coronaviruses, in a human or animal.

In a preferred embodiment, the weight ratio of the totality of the at least one bromelain protease to the totality of the at least one jacalin-related lectin amounts to 50:50 to 0.1:99.9, preferably 40:60 to 1:99, further preferably 30:70 to 2:98, further preferably 20:80 to 3:97, particularly preferably 10:90 to 5:95.

It is further advantageous with the combination preparation in accordance with the invention that at least one bromelain protease is included, preferably the total concentration of all the bromelain proteases in the extract or combination preparation amounting to 0.01 to 50.0 wt %, further preferably 0.1 to 20.0 wt %, particularly preferably 1.0 to 10.0 wt %.

In addition, it is advantageous with the combination preparation if at least one jacalin-related lectin is included, preferably the total concentration of the at least one jacalin-related lectin in the extract amounting to 0.01 to 60.0 wt %, further preferably 1.5 to 50.0 wt %, particularly preferably 2.0 to 30 wt %.

In 1973 Perlstein & Kezdy discovered protease inhibitors in bromelain base powder (BBP) in bromelain that is acquired from the stem of the pineapple plant (Perlstein & Kezdy, Struct., Vol. 1, 249-254). These protease inhibitors were able to inhibit the enzymatic activity of the bromelain proteases from BBP.

Seven isoforms of these bromelain protease inhibitors were originally described in 1973 (Perlstein & Kezdy, Struct., Vol. 1, 249-254). In 1975 Reddy et al completely revealed the primary structure of isoform VII and pointed out the microheterogeneity of the seven isolated isoforms (Reddy et al., J. Biol. Chem., Vol. 250, 1741-1750).

Lenarcic et al. revealed the primary structure of a further bromelain protease inhibitor in 1992 and also revealed an inhibitory effect against cathepsin L (Lenarcic et al., Biol. Chem., Vol. 373, 459-464).

The primary and secondary structures of bromelain protease inhibitor VI was published by Hatano et al. in 1995 (Hatano et al., Eur. J. Biochem., Vol. 232, 335-343). In the following year, the similarity of bromelain protease inhibitor VI with the already described Bowman-Birk trypsin inhibitor was revealed (Hatano et al., Biochemistry, Vol. 35, 5379-5384). The amino acid sequence of all previously described seven isoforms of the bromelain protease inhibitors were finally published by Hatano et al. in 1998 (Hatano et al., J. Biochem., Vol. 124, 457-461).

All the isolation processes of bromelain protease inhibitors previously described in the literature use a two-step chromatographic process. The underlying principle of this method was already published by Perlstein & Kezdy in 1973 (Perlstein & Kezdy, Struct., Vol. 1, 249-254). In the first dimension, i.e. in the first purification step, the chromatographic process of size exclusion chromatography (SEC) is applied. The molecules contained in the BBP can be separated from one another on the basis of their different sizes using SEC. The bromelain proteases (approximately 25 kDA) and the bromelain protease inhibitors (approximately 6 kDa) can in particular be separated thereby.

In accordance with the method of Perlstein & Kezdy, anion exchange chromatography (e.g. weak anion exchange chromatography=WAX) is generally used in a second chromatographic separation. With this method, Perlstein & Kezdy were successful in isolating seven bromelain protease inhibitors (seven different isoforms) from BBP.

When this method is used, a yield of approximately 3 mg of the bromelain protease inhibitor isoform VII or 1 mg of the bromelain protease inhibitor isoform VI from 1 g BBP has been reported. (Reddy et al., Biol. Chem., Vol. 250, 1741-1750; Hatano et al., Eur. J. Biochem., Vol. 232, 335-343).

The purification method that was published by Perlstein & Kezdy and can also be called SEC/WAX has the disadvantage that the isolation of a bromelain protease inhibitor isoform of high purity or in a pure form has not yet been successful.

There is agreement that all previously purified bromelain protease inhibitor isoforms are actually mixtures of different isoforms of bromelain protease inhibitors (Hatano et al., Biol. Chem., Vol. 383, 1151-1156).

The scaling up of the SEC/WAX method is moreover not economical at an industrial scale. What is decisive here is the use of the SEC method in the first dimension, i.e. in the first purification step. Both the capacity and the separation power of the SEC are smaller in comparison with adsorption chromatographic protein purification methods. This becomes particularly clear in the specific case that Hatano et al. have repeated the first SEC step for the insulation of 1 mg bromelain protease inhibitor three times, which represents a substantial time effort even at this small scale (1 g BBP) (Hatano et al. 1995, Eur. J. Biochem., Vol. 232, 335-343).

Since three chromatographic steps are considered the economical upper limit, repeated SEC chromatography is not economical for an industrial application. An SEC column having a volume of approximately 100 liters would have to be used to obtain a yield of approximately 1 g bromelain protease inhibitor using the SEC/WAX method, for example. The SEC/WAX method is consequently uneconomical and not interesting for commercial use both from a technical material aspect and a time economy aspect.

In the case of the purification of bromelain proteases, different methods have been described in the literature (Rowan et al., Arch. Biochem. Biophys., Vol. 267, 262-270; Harrach et al., Protein Chem., Vol. 14, 41-52).

It was therefore also the object of the present invention to provide an improved method for the isolation of bromelain protease inhibitors and bromelain proteases and furthermore to provide a bromelain protease inhibitor and a bromelain protease mixture at high purity and with enriched biological activity.

In a fifth aspect, the invention thus relates to a bromelain protease inhibitor comprising or consisting of at least one peptide having an amino acid sequence that is at least 90%, preferably 95%, particularly preferably 100%, identical with one of the sequences of SEQ ID NO: 1-7, wherein the at least one peptide preferably has a purity of at least 80 wt %, particularly preferably at least 95 wt %, for use in the treatment or prophylaxis of viral infections, caused by coronaviruses, in a human or animal.

In accordance with the invention, a method of purifying at least one bromelain protease inhibitor is equally provided that is characterized in that an aqueous solution containing a dissolved extract from the stem of the pineapple plant at a pH in the range from pH 6.5 to 9.5 is purified by cation exchange chromatography, with the cation exchange material binding bromelain proteases at a pH in this range and the pass of chromatography comprising at least one bromelain protease inhibitor.

The aqueous solution and/or further solutions that can be used in cation exchange chromatography (e.g. an elution buffer) optionally comprises/comprise a buffer substance that has a buffer action in a range from pH 6.5 to 9.5.

Strong or weak cation exchange chromatography (SCX or WCX) can be used for a high capacity and separation power, i.e. cation exchange chromatography in which a strong or weak cation exchange material is used.

The buffer conditions are preferably selected such that in cation exchange chromatography the bromelain protease inhibitors from the extract from the stem of the pineapple plant do not bind to the cation exchange material (cation exchange column) in the first place, but all the bromelain proteases do bind. The bromelain protease inhibitors are consequently located in the pass of the cation exchange chromatography that can be collected and subjected to a further chromatography step.

In a preferred embodiment, the buffer conditions are selected such that the cation exchange chromatography is carried out at a pH of 5.0-10, preferably 7.0-9.5. The aqueous solution in the method can, for example, comprise a buffer substance that is selected from the group consisting of TRIS, HEPES, sodium phosphate, and/or potassium phosphate. In a preferred embodiment, the aqueous solution has weak conductivity. The buffer substance can be contained in the aqueous solution at a concentration of 5-100 mM, preferably 10-50 mM.

The bromelain proteases, that are bound to the cation exchange material, can be released from the cation exchange material and isolated in a further step. This can be done by elution of the bromelain proteases using a suitable elution buffer.

The buffer conditions in the elution buffer are selected such that the binding of the bromelain proteases to the cation exchange material is cancelled. The buffer can have a concentration of 0.01-1.0 M, preferably 0.10-0.5 M, of a salt (e.g. NaCl or KCl). Alternatively, the elution from the cation buffer material can take place via an elution buffer having a pH that is higher than the pH of the aqueous solution or of a washing buffer.

The elution can take place at a step gradient or at a linear gradient. If at least one further purification step of the bromelain proteases is provided, elution preferably takes place with a linear gradient. In this process, in a particularly preferred embodiment, individual fractions of the eluate are isolated. The elution in a step gradient results in a bromelain protease mixture having an enriched biological activity in comparison with the BBP.

The eluate of the cation exchange material contains bromelain proteases that are substantially free of inhibitors. In this respect, the bromelain proteases can contain less than 5.0% (w/w), preferably less than 20% (w/w), further preferably less than 1.0% (w/w), further preferably less than 0.5% (w/w), further preferably less than 0.2% (w/w), particularly preferably less than 0.1% (w/w) bromelain protease inhibitors, with respect to the total peptide mass. The degree of purity of the bromelain proteases can be determined by SEC-HPLC or RP-HPLC.

If the bromelain protease inhibitors are to be further purified, the pass of the cation exchange material that contains bromelain protease inhibitors can be purified in a subsequent second step by anion exchange chromatography (AX), hydrophobic interaction chromatography (HIC), reversed phase HPLC (RP-HPLC), or SEC.

The buffer conditions can be selected here such that at least one bromelain protease inhibitor binds to the anion exchange material, the material of the hydrophobic interaction chromatography, or the material of the RP-HPLC and is then isolated. Except in SEC, the isolation preferably takes place in that washing is done with a buffer and elution is subsequently carried out with a further buffer. This step is not necessary in SEC since the bromelain protease inhibitors do not bind to the SEC chromatography material at all. Suitable buffer conditions (for the binding, washing, and/or elution of peptides or proteins) for the respective materials are known to the person skilled in the art from the prior art.

The term "washing" is familiar to the skilled person. "Washing" is preferably to be understood as the contacting of the chromatography material by a buffer that weakens the bond of unwanted material to the chromatography column, particularly preferably fully cancels it, while the binding of the bromelain protease inhibitors to the chromatography material is maintained.

The elution can take place with a step gradient or a linear gradient, with the eluate optionally being collected in individual fractions.

Depending on the required quality of the bromelain protease inhibitors, a third chromatography step can be carried out subsequent to the second step. A further purification takes place in this third step in which at least one isolated bromelain protease inhibitor is purified via RP-HPLC, AX, or SEC, with the buffer conditions being selected such that at least one bromelain protease inhibitor binds to the material of the RP-HPLC or the anion exchange material and is then isolated. Except in SEC, the isolation preferably takes place in that washing is first done with a buffer and elution is subsequently carried out with a further buffer. Since the bromelain protease inhibitors do not bind to the SEC material, no washing or elution is required (a running buffer is sufficient).

In all the methods in accordance with the invention, the cation exchange material can be selected from the group consisting of strong and weak cation exchangers; the anion exchange material can be selected from the group consisting of strong and weak anion exchangers; the material of the hydrophobic interaction chromatography can be selected from the group consisting of linear, cyclic, non-aromatic and aromatic ligands having a carbon number from C3 to C20; the material of the RP-HPLC can be selected from the group consisting of linear, cyclic, non-aromatic and aromatic ligands (preferably linear ligands) having a chain length from C4 to C18; and the material of the gel filtration chromatography can be a Superdex™ material (e.g. Superdex30Prepgrade from GE Healthcare).

In a preferred embodiment of the method in accordance with the invention, the extract from the stem of the pineapple plant is BBP.

The advantage of the method in accordance with the invention is that a mixture of bromelain protease inhibitor isoforms is obtained that is free of other components of the extract from the stem of the pineapple plant.

It is possible by the method to provide a bromelain protease inhibitor mixture (i.e. the totality of all bromelain protease inhibitor isoforms) in a yield of approximately 1-50% (w/w), preferably 5-30% (w/w), with respect to the starting substance of bromelain base powder (BBP=commercially available extract from the stem of the pineapple plant). Since individual bromelain protease inhibitor isoforms of 0.1% (w/w) or 0.3% (w/w) have been reported in the prior art, this means a big improvement over the prior art for the method in accordance with the invention. The method in accordance with the invention for the isolation of bromelain protease inhibitor isoforms from BBP is consequently considerably more efficient and economical than methods of the prior art.

The provision of individual ultrapure bromelain protease inhibitor isoforms is also possible. This can be achieved in that AX chromatography is performed in the second dimension (=2nd step) and RP-HPLC chromatography in the third dimension (=3rd step). Individual ultrapure bromelain protease inhibitor isoforms can thereby be isolated from an extract from the stem of the pineapple plant.

The present invention comprises a bromelain protease inhibitor comprising or consisting of at least one peptide having an amino acid sequence that is at least 90% identical, preferably 95%, particularly preferably 100%, identical with one of the sequences of SEQ ID NO. 1-7 (sequence of the known bromelain protease inhibitors I-VII).

In accordance with the invention, the at least one peptide in the bromelain protease inhibitor (e.g. at least one isoform of a bromelain protease inhibitor) can have a purity of at least 80 wt %, preferably at least 90 wt %, particularly preferably at least 95 wt %, with respect to contaminating molecules and other bromelain protease isoforms.

A bromelain protease inhibitor can furthermore be provided in accordance with the invention that is a mixture of at least two, preferably at least three, particularly preferably at least four, bromelain protease inhibitor isoforms. The mixture can optionally include all seven known bromelain protease inhibitor isoforms (see SEQ ID NO. 1-7). The mixture of a plurality of bromelain protease inhibitor isoforms has the advantage of an improved effect over individual bromelain protease inhibitor isoforms since a greater range of molecular targets can thus be bound.

In a further preferred embodiment, the bromelain protease inhibitor in accordance with the invention includes at least the bromelain protease inhibitor isoform IV (SEQ ID NO. 4) and/or the bromelain protease inhibitor isoform V (SEQ ID NO. 5).

The mixture can have a purity of at least 80 wt %, preferably at least 90 wt %, particularly preferably at least 95 wt %, with respect to the ratio of bromelain protease inhibitor(s) to contaminating molecules that are not bromelain protease inhibitor (e.g. bromelain proteases).

The at least one peptide in the bromelain protease inhibitor in accordance with the invention can furthermore comprise a) a post-translational modification, preferably glycosylation, characteristic for the pineapple plant; and/or
b) no post-translational modification.

The bromelain protease inhibitor in accordance with the invention can preferably be manufactured in accordance with the method in accordance with the invention.

The bromelain protease inhibitor in accordance with the invention can be used in medicine, preferably in the treatment and/or prevention of a disease that is characterized by intensified expression of at least one cellular protease, preferably at least one cysteine protease.

The invention additionally comprises a mixture of bromelain proteases that contains less than 0.5% (w/w), preferably less than 0.2% (w/w), particularly preferably less than 0.1% (w/w), bromelain protease inhibitors with respect to the total peptide mass. The person skilled in the art can, for example, determine the residual content of bromelain protease inhibitors in a mixture of bromelain proteases via analytical SEC or RP-HPLC.

The bromelain protease mixture in accordance with the invention can be manufactured in accordance with a variant of the method in accordance with the invention.

In a sixth aspect the present invention relates to a bromelain protease mixture that contains less than 5.0% (w/w), preferably less than 2.0 (w/w), further preferably less than 1.0% (w/w), further preferably less than 0.5% (w/w), further preferably less than 0.2% (w/w), particularly preferably less than 0.1% (w/w) bromelain protease inhibitors, with respect to the total peptide mass for use in the treatment or prophylaxis of viral infections, caused by coronaviruses, in a human or animal.

The present invention further relates, in a seventh aspect, to a glycated bromelain protein produced by exogenous non-enzymatic glycation, in particular a glycated jacalin-related lectin, a glycated bromelain protease, a glycated bromelain protease inhibitor, or mixtures thereof, comprising at least one sugar unit covalently bound to the bromelain protein.

The glycated bromelain protein is preferably used in the treatment or prophylaxis of viral infections, caused by coronaviruses, in a human or animal.

A further preferred embodiment hereto provides that the at least one sugar unit covalently bound to the bromelain protein is selected from the group consisting of monomeric or oligomeric hexoses, in particular glucose, galactose, and/or mixtures and combinations thereof.

1 to 10, preferably 1 to 5, particularly preferably 1, 2, or 3 sugar units are covalently bound to the bromelain protein, bound by a Maillard reaction.

The previously named glycated bromelain protein can in particular be manufactured by mixing at least one bromelain protein with at least one reducing sugar and by carrying out a Maillard reaction.

The coronavirus can, for example, be selected from the group consisting of orthocoronaviruses, preferably alphacoronavirus, betacoronavirus, gammacoronavirus, or deltacoronavirus, as well as letoviruses, preferably alphaletovirus, in particular milecoviruse, e.g. microhyla letavirus (MLev-1).

The orthocoronaviruses are here in particular selected form the group consisting of Alphacoronaviruses, selected from the group consisting of colacovirus such as Bat coronavirus CDPHE15; decacovirus such as Rhinolophus ferrumquuinum alphacoronavirus HuB-2013; Duvinacovirus such as human coronavirus 229E, HCov229E); luchacovirus such as Lucheng Rn rat coronavirus; minacovirus such as Ferret coronavirus or Mink coronavirus 1; minunacovirus such as Miniopterus bat coronavirus 1 or Miniopterus bat coronavirus HKU8; myotacovirus such as myotic ricketti alphacoronavirus Sax-2011 or Nyctalus *velutinus* alphacoronavirus SC-2013; pedacovirus such as Porcine epidemic diarrhea virus, (PEDV) or Scotophilus bat coronavirus 512; Rhinacovirus such as Rhinolophus bat coronavirus HKU2 or Swine acute diarrhea syndrome coronavirus (SADS-CoV); Setracovirus such as Human coronavirus NL63 (HCov-NL63) or NL63-related bat coronavirus strain BtKYNL63-9b; Tegacovirus such as alphacoronavirus 1, in particular Canine coronavirus, CCoV, Feline coronavirus, FCoV, or transmissible gastroenteritis virus (TGEV);

Betacoronaviruses selected from the group consisting of sarbecovirus such as severe acute respiratory syndrome related coronavirus ("SARS associated coronavirus"), in particular severe acute respiratory syndrome coronavirus 2 (SARS-CoV-2) and synonymous or non-synonymous mutants hereof, including the variants B.1.1.7, B.1.351, B.1.617, P.1, P.2, B.1.525, B.1.427, B.1.429, L452R, Fin-796H, B.1.526, S:H66D, S:G142V, S:D215G, S:V483A, S:D614G, S:H655Y, S:G669S, S:Q949R, S:N1187D, ORF6:K23–, ORF6:V24–, ORF6:S25–, ORF6:I26–, ORF6:W27–, ORF6:N28–, ORF6:L29–, ORF6:D30–, ORF6:Y31–, S:Y144–, E484K, VOC 20I/484Q, B.1, R.1, A.2.5, C.36, B.1.1.318, B.1.621, B.1.623, severe acute respiratory syndrome coronavirus (SARS-CoV, SARS-coronavirus, also SARS-CoV-1), Embecovirus such as Betacoronavirus 1, in particular bovine coronavirus (BCoV), equine coronavirus (ECoV-NC99), human coronavirus OC43 (HCoV-OC43), porcine hemagglutinating encephalomyelitis virus (HEV), Puffinosis coronavirus (PCoV), human enteric coronavirus (HECoV) China rattus coronavirus HKU24; human coronavirus HKU1 (HCoV-HKU1), Murine coronavirus such as mouse hepatitis virus, MHV), or rat coronavirus (RtCoV); hibecoviru such as. Bat Hp-betacoronavirus Zhejiang2013; merbecovirus (previously MERS-related coronaviruses, MERSr-CoV) such as hedgehog coronavirus 1, Middle East respiratory syndrome-related coronavirus, MERS-CoV), Pipistrellus bat coronavirus HKU5, Tylonycteris bat coronavirus HKU4; Nobecovirus such as Rousettus bat coronavirus GCCDC1 or Rousettus bat coronavirus HKU9; or BatCoV RaTG13, Manis-CoV SRR10168377 and SRR10168378;

gammacoronaviruses selected from the group consisting of cegacovirus such as Beluga whale coronavirus SW1; or igacovirus such as avian coronavirus, in particular turkey coronavirus (Tcov), pheasant coronavirus (PhCoV), infectious bronchitis virus (IBV); and deltacoronavirus, selected from the group consisting of andecovirus such as Wigeon coronavirus HKU20; buldecovirus such as Bulbul coronavirus HKU11 (BuCoV HKU11), coronavirus HKU15, Munia coronavirus HKU13, MunCoV HKU13), white-eye coronavirus HKU16 or thrush coronavirus HKU12, ThCoV HKU12; herdecovirus such as night heron coronavirus HKU19; and moordecovirus such as common moorhen coronavirus HKU21.

In accordance with the invention, the bromelain protease, the jacalin-related lectin, the extract, the combination preparation, the bromelain protease inhibitor, the bromelain protease mixture, or the glycated bromelain protein such as described above are each suitable in accordance with the invention for use in the treatment of symptoms caused by can infection with coronaviruses, in particular fever, coughing, pneumonia, lymphopenic community acquired pneumonia, L-CAP, pleuritis, shortage of breath, indisposition and/or fatigue, sputum, anosmia, and/or ageusia, shortness of breath, muscular and/or inflammations of the throat, joint pain, chest pain, sore throat, headache, backache, ague, nausea, and/or vomiting, colds, diarrhea, coughing blood, lymphopenia, skin rash on hands, feet, or in the mouth, nonsuppurative conjunctivitis at both sides, hypotonia, shock, hypertyrosinemia, dysfunction of the cardiac muscle, inflammation of the pericardium and/or of the cardiac valve, blood coagulation dysfunctions, multisystem inflammatory syndromes in children, MIS-C, and welling of the conjunctiva.

It is of advantage with the previously named extract or combination preparation if the weight ratio of the totality of the at least one bromelain protease to the totality of the at least one jacalin-related lectin amounts to 1:99 to 99.9:0.1, preferably 50:50 to 99:1, further preferably 60:40 to 98:2, further preferably 70:30 to 97:3, further preferably 80:20 to 96:4, particularly preferably 90:10 to 95:5.

The weight ratios or amounts of JRL/bromelain are specified herein such as they occur in the natural product (extract) or when they are used in their natural ratio. A bromelain protease is preferably included, preferably the total concentration of all the bromelain proteases in the extract or combination preparation amounting to 0.1 to 80.0 wt %, further preferably 1.0 to 50.0 wt %, particularly preferably 5.0 to 20.0 wt %.

It is further advantageous with the extract or combination preparation if at least one jacalin-related lectin is included, preferably the total concentration of the at least one jacalin-related lectin in the extract amounting to 0.01 to 50.0 wt %, further preferably 0.1 to 10.0 wt %, particularly preferably 2.0 to 8.0 wt %.

It is of advantage with all of the previously named embodiments if they are included in the form of or as a component of a powder, a granulate, a tablet, in particular a film tablet, a hard capsule, a soft capsule, an effervescent tablet, a solution, in particular an injection solution or an infusion solution, an emulsion, a suspension, a salve, a cream, a past, a gel, a tincture, eye drops, an inhalation powder, a nose spray, a suppository, or a transdermal patch.

It is equally of advantage in all of the previously named aspects of the present invention if the application of the extract, of the bromelain proteases, of the jacalin-related lectin, of the bromelain protease inhibitor, of the bromelain protease mixture, or of the glycated bromelain protein takes place perorally or orally, by intravenous, subcutaneous, or intramuscular injection, by infusion onto the mucous membranes of the nose, of the mouth or of the pharynx, by inhalation, by application onto the surface of the eyes, rectally and/or by means of a transdermal patch.

A further exemplary embodiment for all aspects of the present invention provides that the administration takes place once a week up to once an hour, preferably once a day to 10 times a day, particularly preferably 1 to 3 times a day, or continuously.

BRIEF DESCRIPTION OF THE DRAWINGS

The subject matter in accordance with the invention will be explained in more detail with reference to the following Figures and to the following example without intending to restrict it to the specific embodiments shown here.

FIG. 1 shows the primary structure and molecular mass of previously known isoforms of bromelain protease inhibitors (according to Hatano et al., (2002) Biol. Chem., Vol. 383, 1151-1156);

FIG. 4 shows a schematic overview of the HCov229E test;

FIG. 7 shows lectin with anti-coronavirus activity from the HCoV229E reporter virus screening. The compounds were preincubated for 30 minutes with the HCoV229E virus at a ratio of 1:2 (Table 2) followed by a titration along the target cells. Remdesivir was used as the positive control, DMSO as the negative control. A) Dosage action titration of lectin starting with a 1:500 dilution. The HCoV229E virus infectivity (absolute values) is shown on the left side and the corresponding cell viability (logarithmic values) of the Huh-7.5-FLuc cells is shown on the right side. B) The values of the HCoV229E virus replication and of the cell viability were shown standardized for the 1:500 dilution or the 1:2,500 dilution (red rectangles in A) against the BSA control;

FIG. 15 shows an SDS-PAGE for detecting the proteolytic degradation of the recombinant SARS-CoV-2 spike and of the inhibiting function of HZI 2-07. SARS-CoV-2 spike with bromelain protease (HTI 2-08) and bromelain inhibitor (HZI 2-07) in the quantity of material ratio 1:1:1. 1) PageRuler-Prestained. The rectangle marks the intact spike protein at approximately 150 kDa; the dashed rectangle shows the spike degradation product at approximately 24 kDa;

FIG. 18 shows a total ion chromatograph and a deconvoluted mass spectrograph of recombinant SARS-CoV-2 spike incubated with bromelain protease fraction HZI-2-08 in the quantity of material ratio 100:1, 10 min., 37° C. The arrow marks the intact spike protein at approximately 150 kDA;

FIG. 21 shows a total ion chromatograph and a deconvoluted mass spectrograph of recombinant SARS-CoV-2 spike incubated with bromelain protease fraction HZI-2-08 and bromelain inhibitor HZI 2-07 in the quantity of material ratio 1:1:1, 2 h, 37° C. The arrow marks the intact spike protein at approximately 150 kDA;

DETAILED DESCRIPTION OF THE INVENTION

FIG. 1 shows the primary structure (amino acid sequence) of the seven known bromelain protease inhibitors I, II, III, IV, V, VI, and VII in tabular form. The average and monoisotopic molecular mass in Dalton is furthermore respectively given for every isoform.

Figure 2:
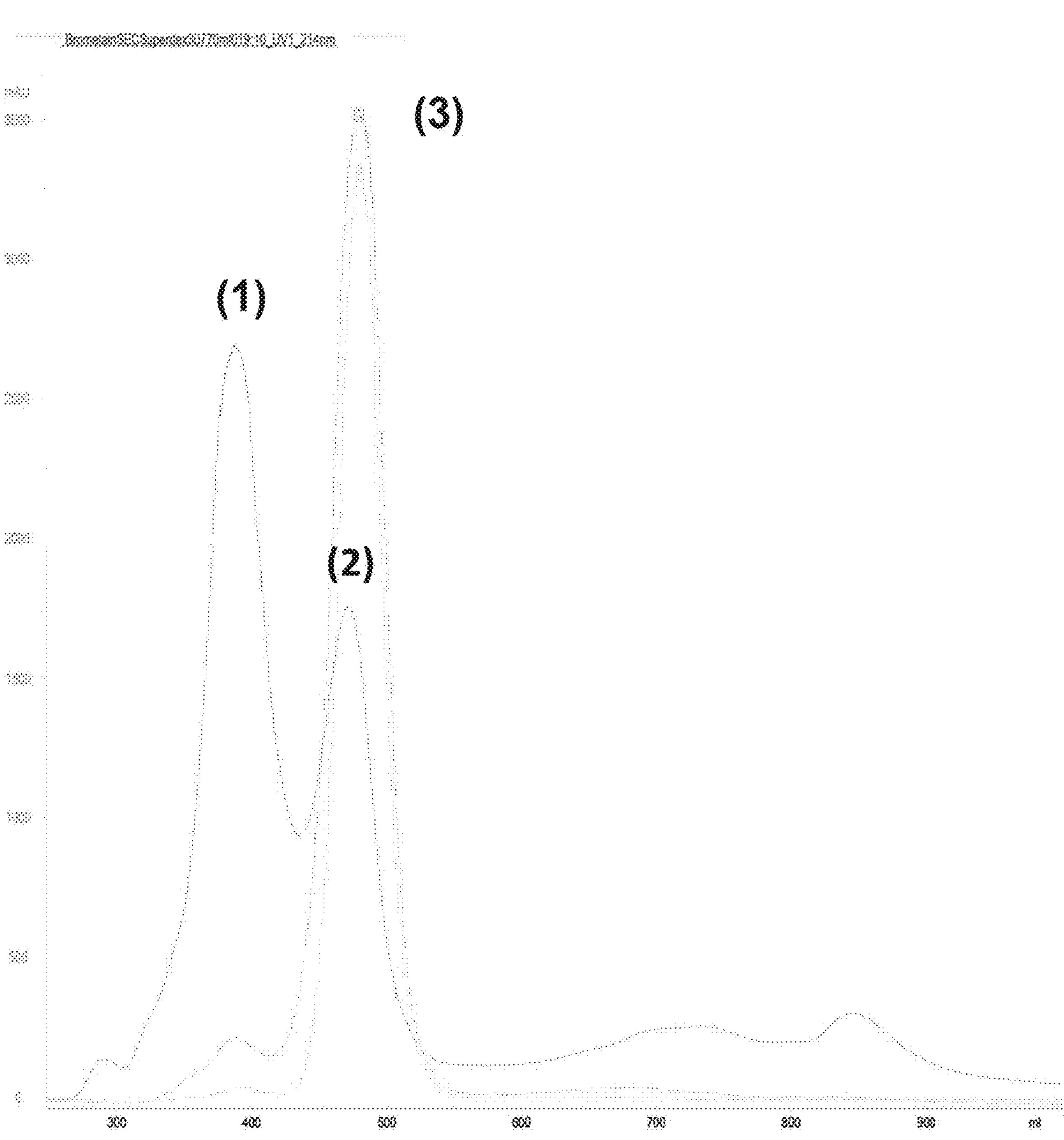
FIG. 2 shows the elution profile of strong cation exchange chromatography (SEC) with BBP.

FIG. 2 shows the elution profile of BBP that was applied to a preparative SEC. The y axis stands for the absorption strength at 214 nm while the x axis reflects the elution volume. The first signal of the elution profile (1) is a component of BBP having a molecular mass of approximately 24 kDa that was identified as bromelain proteases. The second signal of the elution profile (2) is a component of BBP having a molecular mass of approximately 6 kDa that was identified as a mixture of bromelain protease inhibitors. The two signals at (3) are the result of first and second rechromatographies of the pooled fraction of the second signal (2).

Figure 3:
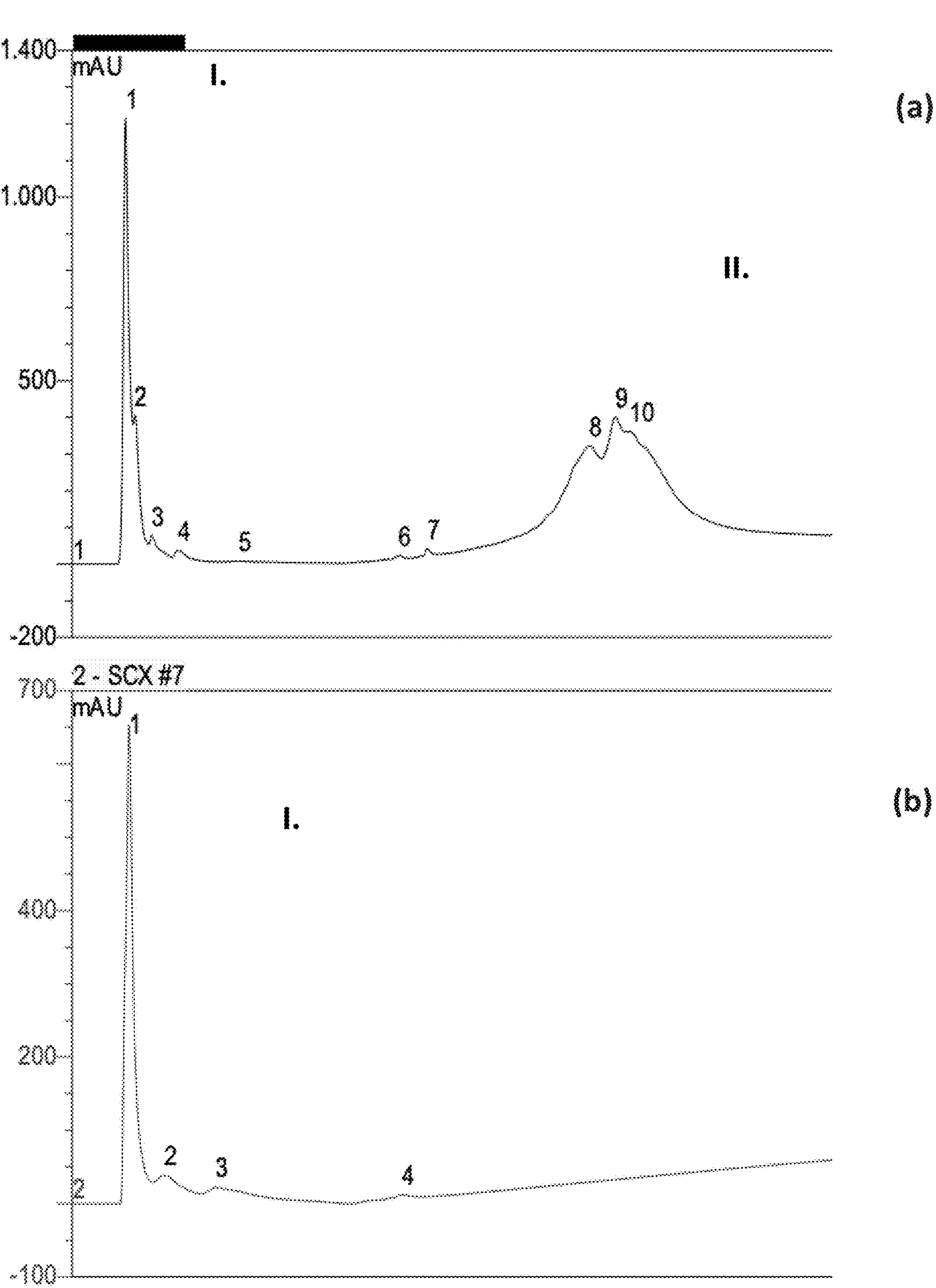
FIG. 3 shows the purification profile of size exclusion chromatography (SCX) with BBP.

FIG. 3(*a*) shows the profile of a purification of BPP over a strong cation exchange column (SCX). The y axis represents the absorption signal at 280 nm while the x axis characterizes the volume of elution buffer. (a) A strong signal occurs in the pass of the SCX column (signal I.), i.e. molecules evidently do not bind to the SX column. These molecules could be identified as bromelain protease inhibitors via SDS-PAGE and mass spectrometry. At a higher volume of elution buffer and a higher ion concentration (linear gradient) a further signal occurs (signal II). The assumption was able to be confirmed by SDS-PAGE and mass spectrometry that they are bromelain proteases here. (b) A rechromatography of the pooled fractions of the first signal (signal I.), that is of the pass of the first chromatography, using the same SCX column under the same conditions as in the first run, demonstrates that the second signal (peak II.) no longer occurs. The bromelain proteases that are responsible for the second signal could thus be separated from the bromelain protease inhibitors.

Example 1

Examination of the Efficacy of Bromelain Over the Alphacoronavirus HCoV229E

1. Sample Preparation

Bromelain was dissolved in TRIS buffered saline solution (TBS) having a pH of 7.3 (10 mg/ml). Dry substances (HZI 2-01 to −03) were dissolved in TBS buffer.

| | |
|---|---|
| Inhibitor manufacture (HZI 2-07) | Note: digestion trials for spike protein |
| Starting material: | Bromelain (Merck, Order #. 1.01651.0025, Batch # K38171251 719) |
| Eluent A: | Dist. water + 0.05% TFA |
| Eluent B: | 60% acetone nitrile for the preparative LC in dist. water + 0.05% TFA |
| Sample solution: | 50 mg/ml bromelain dissolved in dist. water and centrifuged at 9384 g for 15 minutes |
| Separation column: | Jupiter C4 5 μm 300 A, 250 * 10 mm |
| Flow: | 5 ml/min |
| Column volume: | 19.6 ml |
| Sample feed: | 10× after one another per 5 ml of the sample solution |
| Starting conditions: | 6% acetonitrile |
| Gradient: | 20 minutes of 6% acetonitrile on 60% acetonitrile |
| Performance: | The sample feed took place manually on the column equalized with 6% acetonitrile and having a flow rate of 5 ml/min. The column was subsequently flushed with approximately 50-100 ml 6% acetonitrile until approximately the level of the absorption signal prior to the sample application has again been reached. The elution took place by means of a gradient elution of 6-60% acetonitrile over 20 minutes. The peaks occurring during the elution were collected in fractioned form. 10 identical passes with 1 ml sample application each were performed. |
| Lyophilization: | Pooled inhibitor fractions |

The suspension was briefly centrifuged to pelletize the insoluble components. The samples HZI 2-01 and HZI 2-02 were not soluble and were not used for further tests. HZI 2-07 was suspended in 200 mM NaCl 20 mM TRIS pH 8.0.

| | |
|---|---|
| Bromelain enzyme (HZI 2-08) | Note: digestion trials for spike protein |
| Starting material: | Bromelain (Merck, Order #. 1.01651.0025, Batch # K38171251 719) |
| Buffer A: | 50 mM Tris + 150 mM NaCl + 100 mM D-mannose, pH 7.4 |
| Sample solution: | 40 mg/ml bromelain dissolved in buffer A and centrifuged at 9384 g for 15 minutes |
| Separation column: | Superdex 30 prep grade, GE Healthcare, self-packed, 2.5 * 47 cm |
| Flow: | 3 ml/min |
| Column volume: | approx. 230 ml packed |
| Sample feed: | 2 × 5 ml of the sample solution |
| Starting conditions: | Buffer A: |
| Elution: | Isocratically with buffer A |
| Performance: | The sample feed took place manually on the column equalized with buffer A and having a flow rate of 3 ml/min. The pass was carried out isocratically with buffer A. The peaks occurring were collected in fractioned form. Two identical passes with 5 ml sample application each were performed. The collected fractions 2 + 3 of both passes were concentrated to a volume of approximately 5 ml over a 10 kD filtration membrane (Satorius Vivaspin 20) and were subsequently stored in the refrigerator. |
| SEC: | A rechromatography of the concentrated fractions 2 + 3 was carried out by means of SEC. |
| Buffer A': | 50 mM Tris + 150 mM NaCl, pH 7.2 |
| Sample solution: | Concentrated fractions 2 + 3 from both SEC passes (volume approximately 5 ml) |
| Separation column: | Superdex 30 prep grade, GE Healthcare, self-packed, 2.5*47 cm |
| Flow: | 3 ml/min |
| Column volume: | approx. 230 ml packed |
| Sample feed: | 5 ml of the sample solution (conc. Fr 2 + 3) |
| Starting conditions: | Buffer A' |
| Performance: | The sample feed took place manually on the column equalized with buffer A' and having a flow rate of 3 ml/min. The pass was carried out isocratically with buffer A'. The peaks occurring were collected in fractioned form. The collected fractions 2-4 of the pass were pooled. |

Table 1 almost all the sample used together.

TABLE 1

| Sample | Sample description | Concentration | Remarks |
|---|---|---|---|
| Bromelain | Bromelain stem solution in TBS | 10 mg/ml | Bromelain |
| Acm-JRL 1 | Anlec in TBS | 2.2 mg/ml<br>143 μM | Lectin |
| Acm-JRL 2 | Anlec in TBS, Batch 2 | 2.04 mg/ml<br>133 μM | Lectin |

TABLE 1-continued

| Sample | Sample description | Concentration | Remarks |
|---|---|---|---|
| HZI 2-03 | Anlec lyophilizate (Bioaffinity chromatography, D-mannose, dialyzed against glycine, sodium citrate, and citrate, pH 6.9) | ~10 mg/ml; contains larger quantities of citrate | Lectin |
| HZI 2-04 | Anlec in TBS (Bioaffinity chromatography, D-mannose, dialyzed against 2 l water, dialyzed against 50 mM TBS buffer, concentrated with 5 kDa membrane) | 1.77 mg/ml 115 μM | Lectin |
| HZI 2-05 | Anlec in TBS (Bioaffinity chromatography, D-mannose, dialyzed against 2 l water, dialyzed against 50 mM TBS buffer, concentrated with 5 kDa membrane) | 4.22 mg/ml 336 μM | Lectin |
| HZI 2-06 | Anlec in dist. water (bioaffinity chromatography, D-mannose, hydrophobic interaction chromatography C6, concentrated with 5 kDa membrane) | 2.9 mg/ml 188 μM | Lectin |
| HZI 2-07 | Bromelain inhibitor lyophilizate (RP-HPLC C4, freeze dried) | 1.05 mg/ml | Inhibitor |
| HZI 2-08 | Protease mixture in mM TRIS + 150 mM NaCL pH 7.2 (size exclusion chromatography) | 1.14 mg/ml | Protease mixture |
| HZI 2-09 | Anlec in TBS (Bioaffinity chromatography, D-mannose, dialyzed against 50 mM TBS buffer, concentrated with 5 kDa membrane) | 2.2 mg/ml 143 μM | Lectin |
| HZI 2-10 | Anlec in TBS (Protease inhibitor with MMTS, bioaffinity chromatography, D-mannose, dialyzed against 50 mM TBS buffer, concentrated with 5 kDa membrane) | 3.6 mg/ml 234 μM | Lectin |

MMTS: Methyl methanethiosulfonate;
RP-HPLC: reversed-phase high performance liquid chromatography;
TBS: TRIS buffered saline solution (pH 7.3)

2. Performance of the Tests for Antiviral In Vitro Activity of Bromelain, Fractions, and Lectin Against HCoV229E Bromelain and lectin were dissolved in TBS. The suspension was briefly centrifuged to pelletize the insoluble components. Firefly luciferase expressing Huh 7.5 FLuc cells were cultivated in DMEM medium (Gbico #41965-039)+10% fetal calf serum (FCS)+1% penicillin/streptomycin+1% L-glutamine+2% non-essential amino acids (=DMEM complete)+5 mg/ml blasticidin. $2\times10^4$ cell/well (96 well plate) were completely sowed in 100 μl DMEM 24 h before the experiment.

The alphacoronavirus HCoV229E that contains a renilla luciferase (RLuc) was preincubated with the compounds at RT in a ratio of 10:1 (90 μl virus+10 μl compound) for 30 min. The titer of the virus stock solution amounted to $3.41\times10^6$ TCID50/ml (virus concentration at which 50% of the cells are infected per ml for all the experiments. Corresponds here to the number of infectious particles per ml.). The mixture was diluted in media and titrated on target cells in 1:5 steps after the preincubation. FIG. 4 shows a schematic representation of the test performance for the alphacoronavirus CoV229E.

The preincubation was carried out in a ratio of 1:2 (10 μl virus+10 μl compound) for further experiments. Firefly luciferase expressing Huh 7.5 FLuc cells were infected with HCoV229E one day after the sowing in the presence of the specified concentrations of the compound [serial titration (1:5) of the cells]. The viral starting dilution amounted to 1:500, based on the starting concentration in the original sample and are shown in Table 2. The specifications for the bromelain sample having the stock concentration 10 mg/ml are analog to the sample HZI 2-03 and are not shown separately.

TABLE 2

| Bromelain and lectin concentrations for the HCoV229E test | | | | | |
|---|---|---|---|---|---|
| | Acm-JRL 1 | HZI 2- 03 | HZI 2- 04 | HZI 2- 05 | Bromelain 2 mg/ml |
| Concentration of stock solution | 2.2 mg/ml 143 μM | 10 mg/ml | 1.77 mg/ml 115 μM | 4.22 mg/ml 336 μM | 2 mg/ml |
| 1:10 predilution | 0.22 mg/ml 14.3 μM | 1 mg/ml | 0.177 mg/ml 11.5 μM | 0.422 mg/ml 33.6 μM | 0.2 mg/ml |
| 1:2 predilution | 1.1 mg/ml 71.5 μM | 5 mg/ml | 0.885 mg/ml 57.5 μM | 2.11 mg/ml 168 μM | 1 mg/ml |
| Serial dilution 1:500 | 0.0044 mg/ml 0.286 μM | 0.02 mg/ml | 0.0035 mg/ml 0.23 μM | 0.0084 mg/ml 0.672 μM | 0.004 mg/ml |
| Stock solution HCoV229E | $3.41\times10^6$ TCID50/ml | $3.41\times10^6$ TCID50/ml | $3.41\times10^6$ TCID50/ml | $3.41\times10^6$ TCID50/ml | $3.41\times10^6$ TCID50/ml |

TABLE 2-continued

Bromelain and lectin concentrations for the HCoV229E test

| | Acm-JRL 1 | HZI 2- 03 | HZI 2- 04 | HZI 2- 05 | Bromelain 2 mg/ml |
|---|---|---|---|---|---|
| 1:10 predilution (90 μl virus + 10 μl compound) | $3.1 \times 10^6$ TCID50/ml → per ml: $3.1 \times 10^6$ virus particles on 0.22 mg compound | $3.1 \times 10^6$ TCID50/ml → per ml: $3.1 \times 10^6$ virus particles on 1 mg compound | $3.1 \times 10^6$ TCID50/ml → per ml: $3.1 \times 10^6$ virus particles on 0.177 mg compound | $3.1 \times 10^6$ TCID50/ml → per ml: $3.1 \times 10^6$ virus particles on 0.422 mg compound | $3.1 \times 10^6$ TCID50/ml → per ml: $3.1 \times 10^6$ virus particles on 0.2 mg compound |
| 1:2 predilution (10 μl virus + 10 μl compound) | $1.705 \times 10^6$ TCID50/ml → per ml: $1.75 \times 10^6$ virus particles on 1.1 mg compound | $1.705 \times 10^6$ TCID50/ml → per ml: $1.75 \times 10^6$ virus particles on 5 mg compound | $1.705 \times 10^6$ TCID50/ml → per ml: $1.75 \times 10^6$ virus particles on 0.885 mg compound | $1.705 \times 10^6$ TCID50/ml → per ml: $1.75 \times 10^6$ virus particles on 2.11 mg compound | $1.705 \times 10^6$ TCID50/ml → per ml: $1.75 \times 10^6$ virus particles on 1 mg compound |

TCID50/ml: Virus concentration at which 50% of the cells are infected per ml. Corresponds here to the number of infectious particles per ml.

48 h after the inoculation and incubation of the cells at 33° C. and 5% $CO_2$, the virus inoculum was removed and the cells were washed twice in phosphate buffered saline solution (PBS) and lyzed in 50 μl PBS/0.5% Triton X-100. The lysis of the cells was further amplified by freezing the plates at −20° C. 20 μl of the lyzate were used for the measurement of the cell viability via the firefly luciferase signal and a respective 20 μl of the lyzate were used for the analysis of the virus replication/infection efficiency via the renilla luciferase signal.

3. Results of the Tests for Antiviral In Vitro Activity of Bromelain, Fractions, and Lectin Against HCoV229E Bromelain and lectin batches were first tested by a HCoV229E renilla luciferase reporter virus, an alpha coronavirus, using Huh-7.5-FLuc cells that are highly permeable for an HCoV229E infection. These cells are designed such that they express a firefly luciferase reporter gene, which makes the evaluation of the cell viability in a dual luciferase reporter assay possible. All the lectin samples consisted of different isolates of the lectin from bromelain. Samples HZI 2-01 and 2-02 were not used due to the insolubility. Bromelain was used as the control in concentrations of 2 mg/ml or 10 mg/ml.

Figure 5:
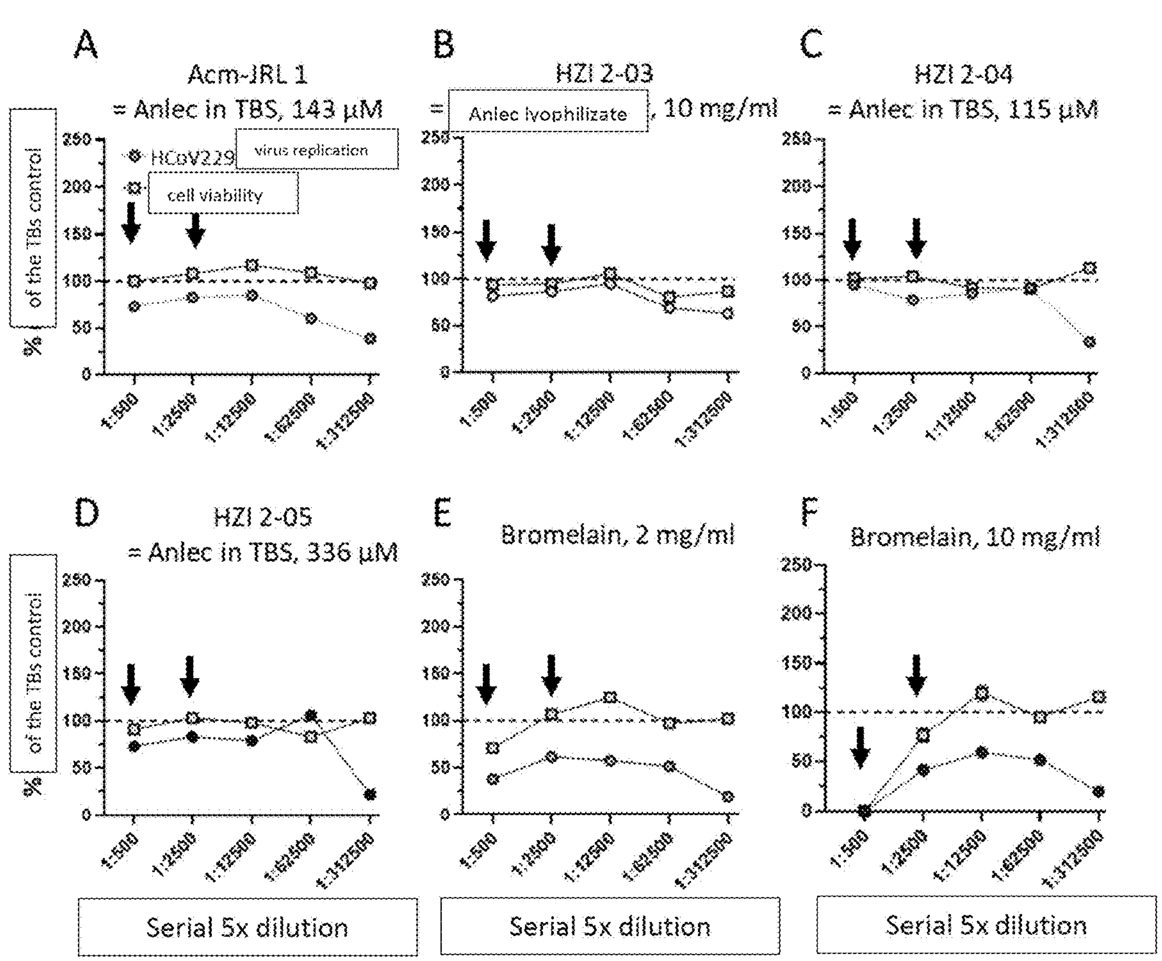
FIG. 5 shows lectin with anti-coronavirus activity from the HCoV229E reporter virus screening; shows bromelain and lectin with anti-coronavirus activity from the HCoV229E reporter virus screening; A) to F) The compounds (starting concentrations are specified) were preincubated with the HCoV229E virus in a ratio of 1:10 for 30 minutes (Table 2) followed by serial titration on the target cells Huh-7.5-FLuc and an incubation for 48 h. The activity of RLuc and FLuc was measured as a measure for the residual infectivity and cell viability. The data were standardized to the TBS control. The black arrows mark the 1:500 dilution or the 1:2500 dilution that were applied standardized in FIG. 6.

It was able to be demonstrated that bromelain and lectin displayed a promising antiviral activity against the HCoV229E reporter virus (FIG. 5).

Figure 6:
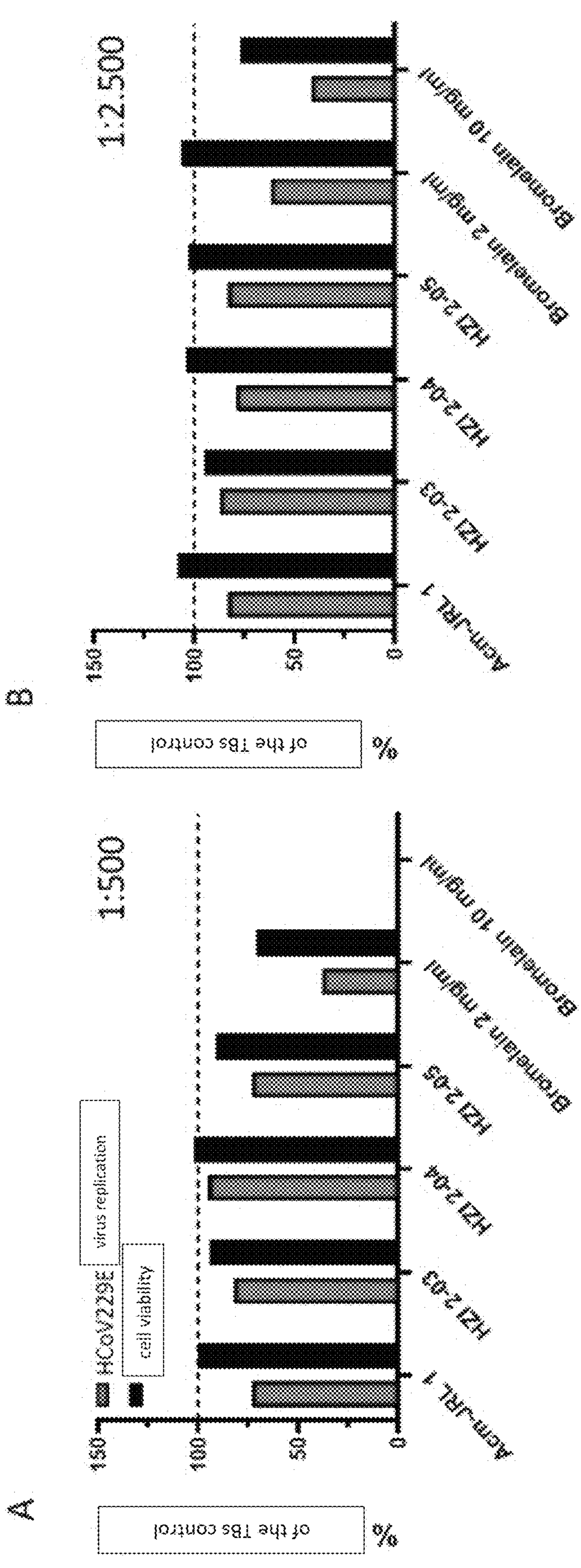
FIG. 6 shows lectin with anti-coronavirus activity from the HCoV229E reporter virus screening. The compounds were preincubated for 30 minutes with the HCoV229E virus at a ratio of 1:10 (Table 2) followed by a titration along the target cells. A) The values of the HCoV229E virus replication and of the cell viability were shown standardized for the 1:500 dilution (black arrows in FIG. 5) against the TBS control. B) Standardized representation of the 1:2,500 dilution.

High concentrations of bromelain (FIG. 5E and FIG. 5F) resulted in a small cell viability. At 100% cell viability (indicated by the dashed line), an approximately 50% reduction (round dots) of the virus replication of the alphacoronavirus HCoV229E was able to be observed for bromelain. The black arrows mark the 1:500 dilution or the 1:2500 dilution that were applied standardized in FIG. 6; The 1:2,500 dilution shows a smaller cytoxicity per se due to the reduced compound concentration, whereby any occurring antiviral effects—and thereby also an improved cell viability—can be better demonstrated.

A virus replication reduced by approximately 25% can also be recognized at the 1:500 dilution on a standardization of the results with approximately 100% cell viability in the samples Acm-JR 1 and HZI 2-05. HZI 2-03 shows an approximately 20% reduction, whereas HZI 2-04 is inactive. Bromelain is accompanied at both concentrations (2 and 10 mg/ml) by a great reduction of the cell viability so that valid conclusions cannot be drawn on a reduction of the virus replication. The reduction of the cell viability is mainly caused by the protease activity of the bromelain, whereby a detaching of the cells from the well base takes place. The subsequent luciferase assay only includes the adherent cells and does not provide a differentiation of dead and vital cells floating in the culture medium, whereby a false result of the cell viability occurs.

A reduction of the virus replication of approximately 20-25% can be recognized in the 1:2,500 dilution in all lectins at approximately 100% cell viability. Bromelain even shows an approximately 45-50% reduction with a cell viability >100% at a stock concentration of 2 mg/ml. Only the highly concentrated bromelain having a stock concentration of 10 mg/ml shows a reduced cell viability so that valid conclusions cannot be drawn on a reduction of the virus replication. However, a drop in the virus replication can also be documented here.

The results should be confirmed by the lectins in a further trial. In addition, the antiviral action should be amplified with a higher substance to virus ratio in the preincubation (1:2 instead of 1:10). The starting concentrations of the titration 1:500 are furthermore set to correspond to the first pilot trials. The samples Acm-JRL 1, HZI 2-03, and HZI 2-05 were used for the experiment. Remdesivir (1 m in TBS), DMSO (1:40 in TBS), and BSA (5 mg/ml in TBS) were used as controls (FIG. 7A).

The positive control remdesivir brings about a complete reduction of the virus replication. At the 1:500 dilution, the lectins Acm-JRL 1 and HZI 2-05 displayed moderate antiviral effects on the HCoV229E reporter virus (FIG. 7B) while HZI 2-03 had no antiviral effect. The samples Acm-JRL 1 and HZI 2-05 displayed an approximately 25% reduction of the HCoV229E virus replication at >100% cell viability. If the 1:2,500 dilution is looked at, sample HZI 2-05 displayed a 50-60% reduction of the virus replication at >100% cell viability.

The results of the preceding trial were able to be confirmed by this trial. A further reduction of the virus replication in sample HZI 2-05 was able to be achieved by a higher concentration of the lectins [ratio 1:2 approximately 50-60% reduction vs. 1:10=approximately 20$ reduction HCoV229E replication (shown in FIG. 6B)]

It was able to be shown that an infection by the HCoV229E can be prevented in the in vitro trial.

Example 2

Isolation of the Samples HZI 2-09 and HZI 2-05

Figure 8:
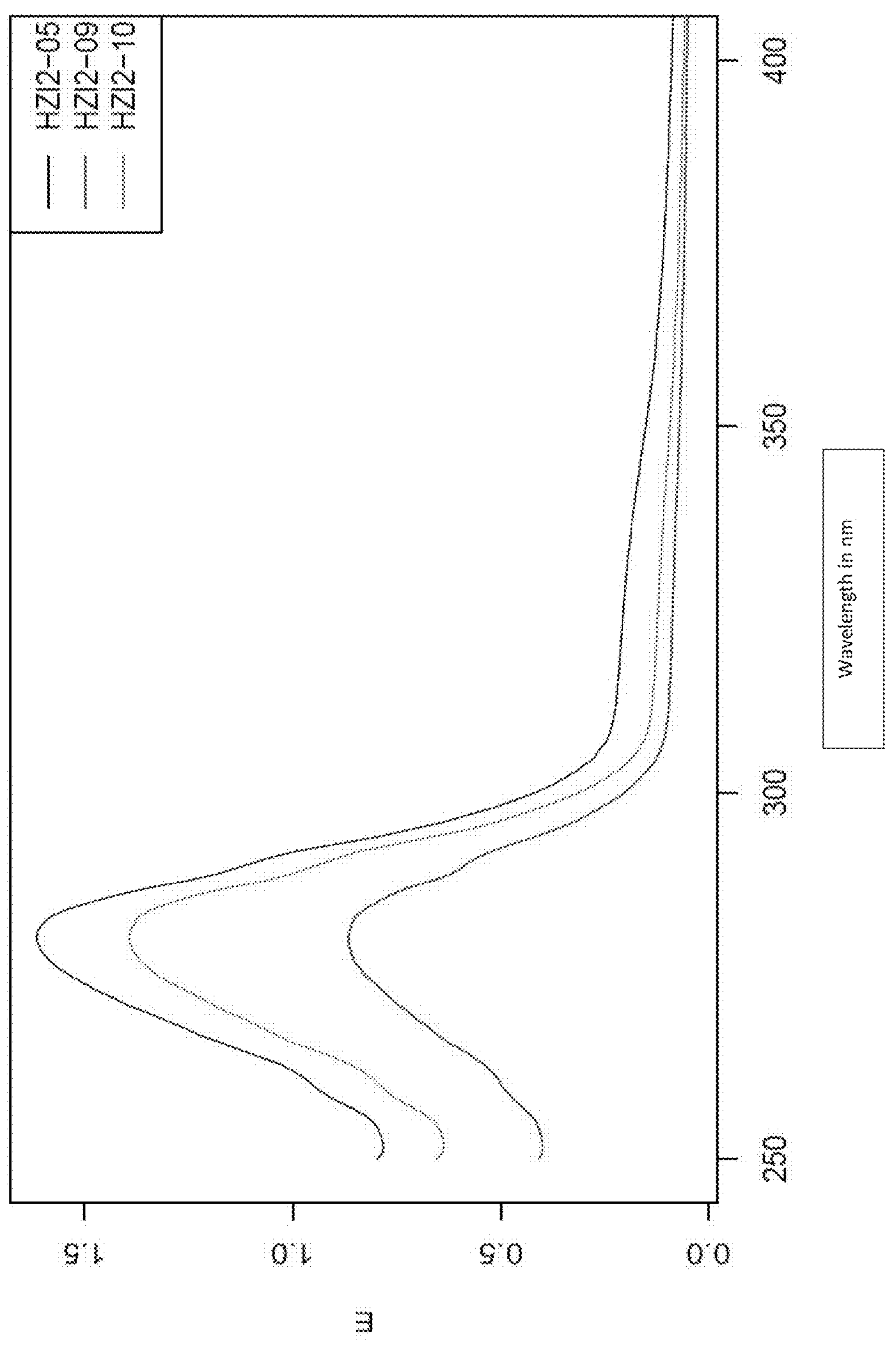
FIG. 8 shows exemplary UV/VIS spectra of various manufactured anlec batches.
Figure 9:
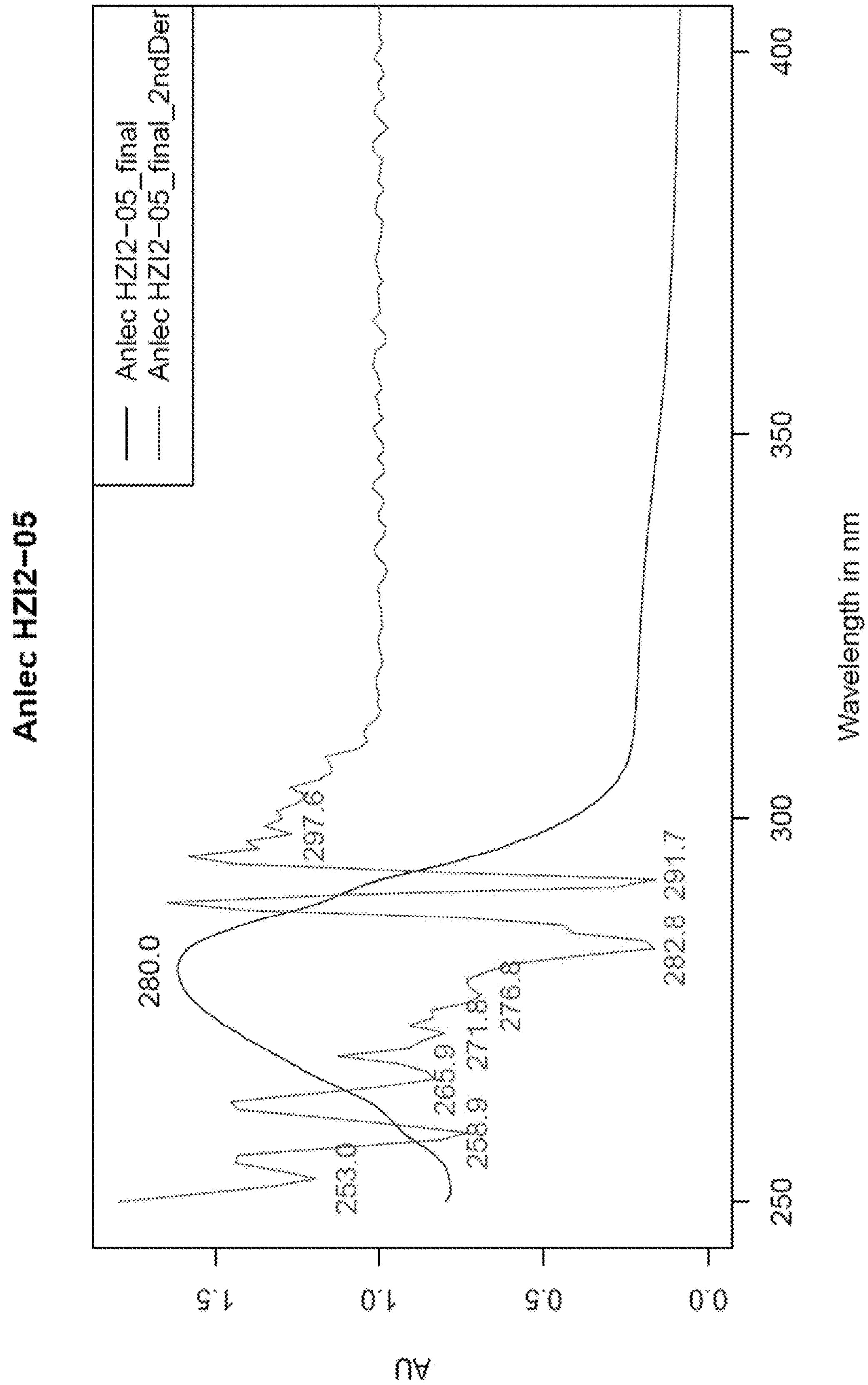
FIG. 9 shows a detailed evaluation of an exemplary anlec UV/VIS spectrum by forming the second derivation. The maximum of the UV/VIS spectrum is at 280.0 nm; significant subbands are shown in red; they correspond to the typical absorption layers of the aromatic amino acids Phe, Tyr, and Trp.

1200 mg Bromelain (Merck, Order #. 1.01651, Batch #K38171251719) are dissolved in 30 ml buffer A (50 mm TRIS, 500 mM NaCl, pH 7.2) at 40 mg/ml and are centrifuged at 9000 g for 15 min. A 5 ml aliquot of this solution is loaded at a flow of approximately 2 ml/min on a D-mannose agarose chromatography column of the dimensions 10×50 mm (pack volume 4 ml) linked covalently that had previously been equalized with buffer A. The column is flushed with at least 25 CV ("column volumes") until the original base line has again been reached or a constant base line has been obtained. The elution of the anlec now takes place by switching to buffer B (50 mM TRIS, 500 mM NaCl, 1 M D-mannose, pH 7.2); the fraction is collected. This application in 5 ml aliquots is repeated multiple times, e.g. five times. The eluted and collected fractions are pooled and are filled with MWCO 3.5 kDa in a dialysis tube. The fraction size of an elution amounts to approximately 7 ml. The dialysis takes place against 2 l buffer C (50 mM TRIS, 150 mM NaCl, pH 7.2) under steady stirring at room temperature or at 4° C. with multiple buffer changing until the mannose concentration by dialysis amounts to ≤1 mM. Flocculation is separated by centrifuging or filtration after the dialysis. The excess is reduced to a smaller volume by means of an ultrafiltration membrane having MWCO 5 kDA or less so that the original protein concentration after the dialysis is increased to a multiple. The protein concentration in a first approximation by means of the UV absorption can be calculated at 280 nm, e.g. by means of a theoretically calculated molar extinction coefficient for anlec in accordance with www.uniprot.org, as was done here. Typical UV/VIS spectra for exemplary batches are shown in FIG. 8, a detailed evaluation by forming the second derivation is shown in FIG. 9.

Figure 10:
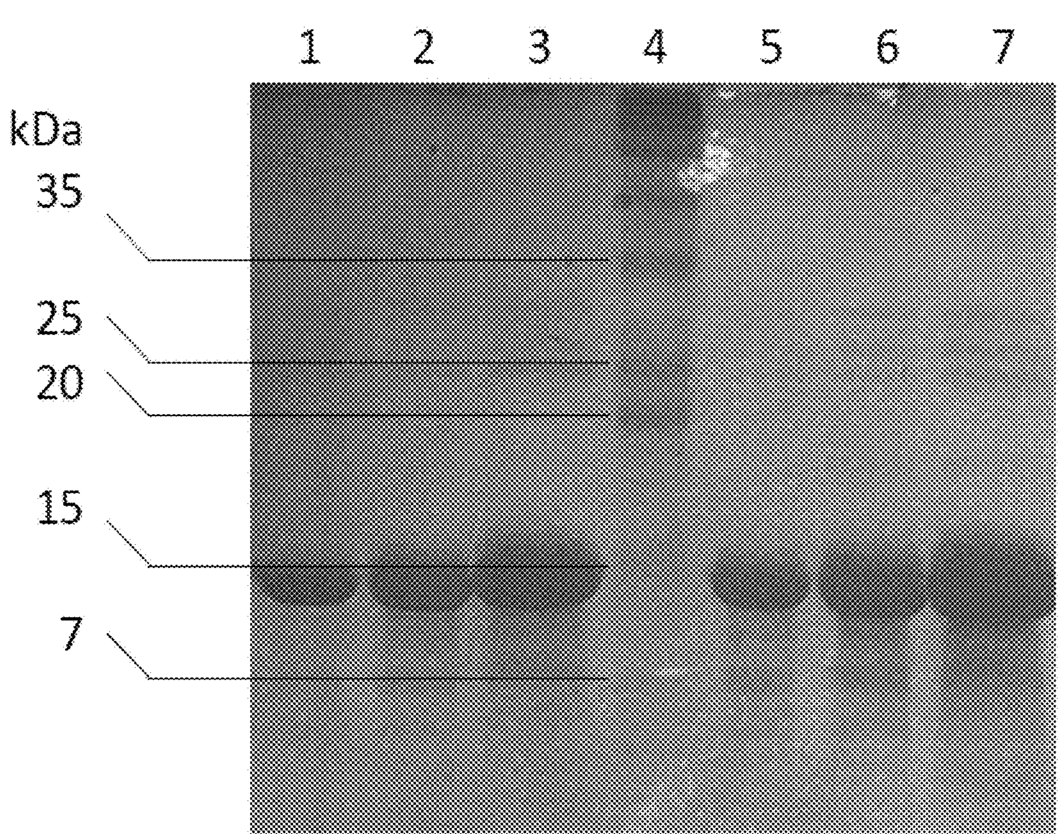
FIG. 10 shows an SDS-PAGE analysis of representative lectin batches. There are shown: lanes 1-3: (5.6/11.1/22.2) μg HZI 2-09. Lane 4: 4.5 μl SERVAChrom Protein Standard III. lanes 5-7: (8.9/17.8/35.6) μg HZI 2-10. (T=14%, C=5%; samples were reduced before application with DTT and were heat denatured while adding SDS at 95° C. for 3 min.)

The results of an electrophoretic analysis by means of SDS-PAGE exemplary anlec batches are shown in FIG. 10. The two batches show a main band at approximately 15 kDA and a plurality of subbands; these subbands can in particular be recognized by the heavy gel overload in lanes 3 and 7.

Figure 11:
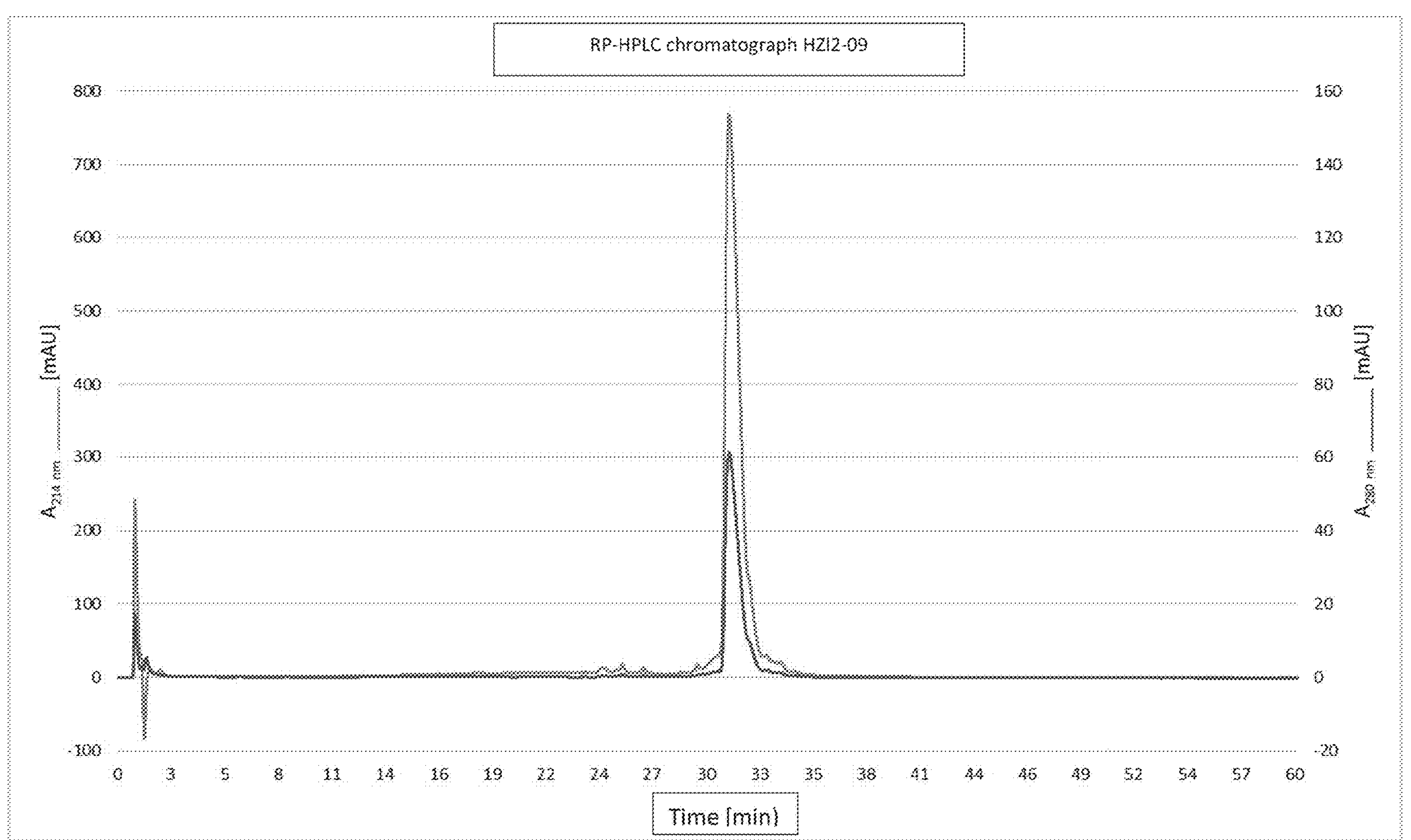
FIG. 11 shows an RP-HPLC UV-chromatograph of the anlec batch HZI 2-89. Detection of the absorption at $\lambda$=214 nm (blue) and $\lambda$=280 nm (red)

An RP-HPLC analysis of a representative batch is shown in FIG. 11; the main mass 1 was determined by LC-MS coupling and a calculation via deconvolution at 15.388 Da (approximately 15.38 kDa). +162 Da species could furthermore also be measured that indicate glycated proteins, see Gross et al. (2020) J. Pharm. Biomed. Anal. 181, 113075.

Example 3

Examination of the Binding of Bromelain with Respect to the Spike Protein of the SARS CoV-2 Virus.

1. Sample Preparation 1.1 Cloning, Expression, and Purification of the SARS-CoV-2 Spike Protein The nucleotide sequence of the extracellular domains of the SARS-CoV-2 spike protein (1-1213) was acquired as a synthetic gene from Eurofins MWG. The gene was amplified by means of PCR and was provided with the restriction interfaces 5'-BamHI/XhoI-3'. The gene was subsequently tied up by sticky end cloning by means of T4 DNA ligase in the eucaryotic expression vector pCAGGS (BamHI tied up again). The expression of the spike protein was carried out in HEK293 cells. For this purpose, HEK293 cells were completely cultivated in a hyperflask (growth area 1720 $cm^2$) up to a confluence of 80-90% in DMEM (37° ° C., 5% $CO_2$). The transfection was subsequently carried out with a 1:2 ratio of pCAGGS spike protein:polyethyleneimine (linear, average molecular weight 25,000 Da). The DNA-PEI solution was removed after 5 hours and completely replaced with DMEM. The cells were cultivated for a further 48 h at 37° C. and 5% $CO_2$ before the culture excess was harvested.

The culture excess was applied to a 5 ml GHisTrap HP column to purify the SARS-CoV-2 spike protein. After a thorough washing with lysis buffer (200 mM NaCl, 20 mM TRIS pH 8.0, 20 mM imidazole), the protein was eluted with elution buffer (200 mM NaCl, 20 mM TRIS pH 8.0, 500 mM imidazole). The acquired protein was subsequently further separated via a HiLoad 16/600 Superdex 200 PG and the peak was collected with an elution volume of 60-70 ml.

1.2 SPR Binding and Affinity Test

The binding kinetics and affinity tests of lectins were carried out on a Biacore X100 system (GE Healthcare). The purified extracellular domain of the spike protein (1-1213) and of the ACE-2 receptor (Sigmal Aldrich, #SAE0064) was covalently immobilized at a CM5 sensor chip via amino-coupling in 10 mM sodium acetate buffer (pH 4.5) for a final 9600 for the spike and 4000 for the ACE-2 receptor. Surface plasmon resonance spectroscopy (SPR) assays were carried out at a flow rate of 30 μl/min in 1×HBS-EP (150 mM NaCl, 10 mM HEPES pH 7.4, 3 nM EDTA, 0.005% Tween-20). Increasing concentrations of lectin (1.25 to 20 M) for spike were injected for single cycle measurements (120 s contact time, 180 s dissociation time).

1.3 SARS-CoV-2 SDS-PAGE and LC-MS Analytics

The glycolization of the recombinantly acquired spike was demonstrated enzymatically: 20 μg SARS-CoV-2 spike in 200 mM NaCl solution and 20 mM TRIS pH 8.0. Buffering was carried out with 2 μl (1000 IU) PNGAse F and the associating buffering was carried out in accordance with the manufacturer's protocol of New England Biolabs®, Inc. and incubated at 37° C. for 6 h. The lyophilizate of the bromelain inhibitor (HZI 2-07) was buffered and suspended in 200 mM NaCl solution with 20 mM TRIS pH 8.0. The Eppendorf vessel was centrifuged with the suspension for the pelletization of the insoluble components and the content of the solution was photometrically determined. To detect the proteolytical degradation of the recombinant SARS-CoV-2 spike and of the peptide product fragment sizes produced therefrom and of the inhibitory function of the HZI 2-07, recombinantly produced SARS-CoV-2 spike was mixed with bromelain protease HZI 2-08 and without inhibitor HZI 2-07 in stoichiometric ratios and was incubated at 37° C. The sample extraction for SDS-PAGE or LC-MS analytics took place as follows:

The sample was admixed with SDS dye (1.2 g SDS, 6 mg bromophenol blue, 4 ml glycerol, 0.6 ml 1 M TRIS pH 8.0, 5.4 ml $H_2O$ heated to dissolve all the components; 930 mg dithiotheitol (DTT) were then added to acquire a 6×SDS dye buffer) and immediately boiled at 100° ° C. for 2-3 min.

Sample extraction for LC-MC analytics: The sample was immediately frozen in liquid nitrogen, stored at −80° C., and thawed on ice a few minutes before the LC-MS measurement.

The SDS-PAGE with 12% v/v polyacrylamide portion was loaded with 10 μl of the prepared samples. 6 μl "PageRuler Prestained Protein Ladder" (Thermo Fisher Scientific) was loaded to monitor the progress of the SDS-PAGE and to estimate the approximate amount of the separated proteins after the dyeing of the gel. The electrophoresis was carried out in a "Mini-PROTEAN® Tetra System" (BIO RAD) with an SDS Laemmli buffer at a voltage of 140 V for 90 min. After the termination of the electrophoresis the SDS-PAGE was heated in a microwave oven with a dye solution (Coomassie Blue 0.05% m/v, methanol 50% v/v, pure acetic acid 7% v/v, water 43% v/v) and stored in water for 24 h before the photodocumentation took place.

The direct intact protein UPLC-ESI-MS analysis was carried out over an UltiMate 3000 UPLC system coupled with a Maxis4G Q-TOF mass spectrometer with an Apollo II ESI source. Measurement took place in the positive mode. The samples were separated via an Aeris Widepore XB-C8 column (3.6 μm, 150×2.1 mm; Phenomenex). The separation took place at a flow rate of 0.3 ml/min (eluent A: deionized water with 0.1% V/V acetic acid, eluent B: distilled acetonitrile with 0.1% v/v acetic acid) at 45° C. with a gradient of 2% B for 30 s, followed by a linear gradient up to 75% B in 10 min and a constant of 75% B for a further 3 min. The flow rate was throttled to 75 μl/min before entering the ion source. Mass spectra were generated in the centroid mode of 150-2500 m/z at 2 Hz. The mass spectrometry ion source parameters amounted to: 500 V end plates offset, 4000 V capillary voltage, 1.1 bar nebulizer gas pressure, 6 l/min dry gas flow, and 180° C. drying temperature. Protein masses were summed via the total ion chromatograph from the retention time period 6.5 min to 9 min for the bromelain protease fraction (HZI 2-08) assays with and without bromelain inhibitor (HZI 2-07) for the total ion chromatographs to demonstrate the glycolsylization of 7.0-7.6 min and were deconvoluted with an instrument resolving power of 8000 to the maximum entropic deconvolution algorithm at high resolution with Compass DataAnalysis to natural masses.

2. Results 2.1 SARS-CoV-2 Spike Protein Binding Assay

SARS-Co-2 spike protein binding assays were carried out with the aid of SPR in vitro for the lectins differently isolated from the bromelain. Purified SARS-CoV-2 spike protein was immobilized by aminocoupling on a Cm5 chip for this purpose. The jacalin-related lectins were subsequently tested for their binding; their dissociation constant and their binding kinetics were determined. In this respect, different binding characteristics and on-off rates were observed, which is shown in more detail in the following.

Figure 12:
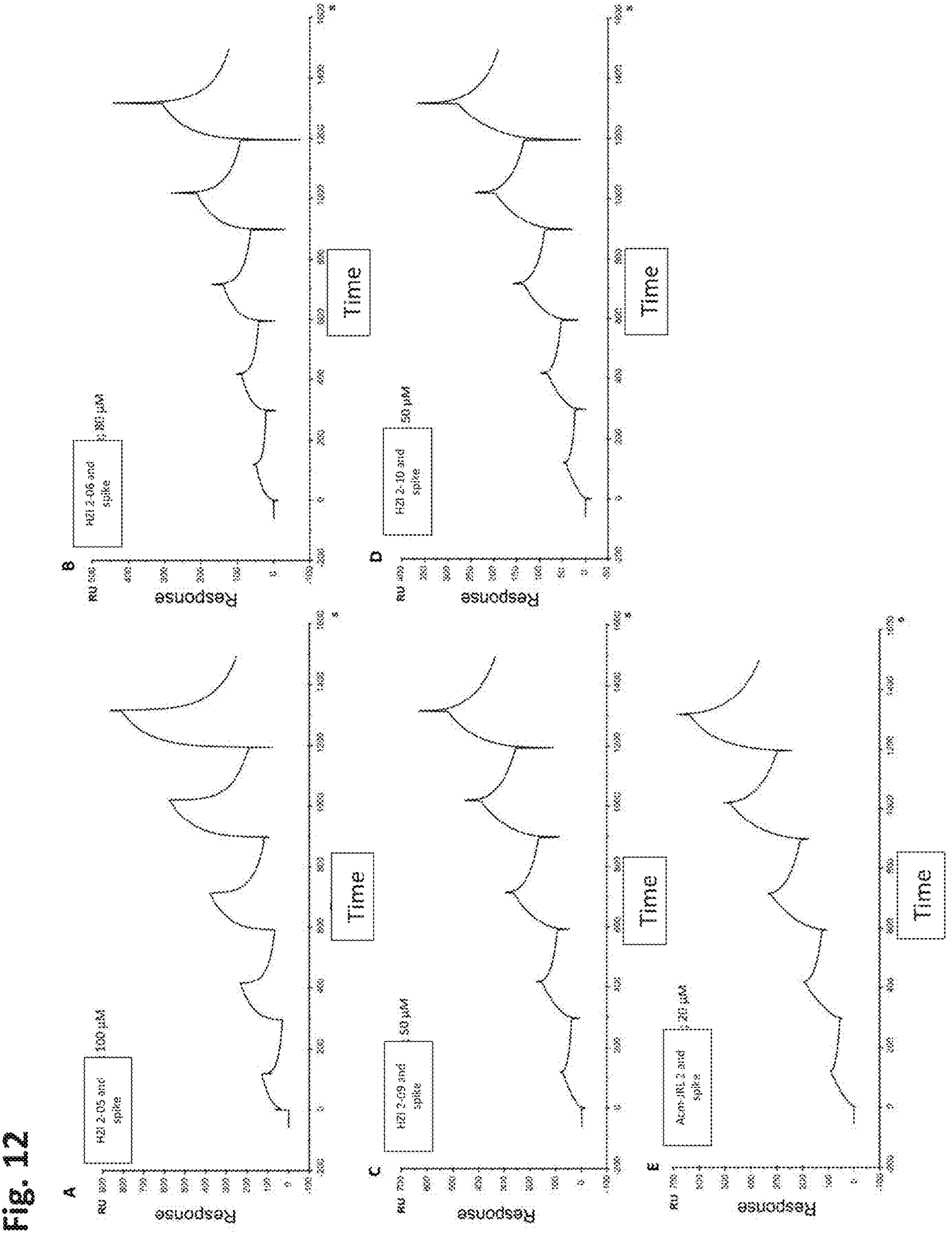
FIG. 12 shows surface plasmon resonance spectroscopy (SPR) binding kinetics and an affinity test for SARS-CoV-2-spike protein and different lectin batches isolated from bromelain A) HZI 2-05, (B) HZI 2-06, C) HZI 2-09, D) HZI 2-10, and E) Acm-JRL 2). Increasing concentrations of the ligand (highest concentration: A) 100 μM, B) 80 μM, C+D) 50 M, E) 20 μM, starting therefrom 5 1:1 dilutions) were injected for single cycle measurements. The sensorgraph shows a faster binding than dissociation of the lectins to the spike protein (on-off rate). The surface containing the spike protein was regenerated with 80% ethylene glycol between the individual batches.

Different batches of the bromelain isolated lectin (HZI 2-05, HZI 2-06, HZI 2-09, HZI 2-10, and Acm-JRL 2) were examined as to their characteristics within the binding assay by means of SPR. In this respect, slight differences of the batches were able to be determined, with above all the association and dissociation rates being changed. It was able to be observed here that the bound lectin at HZI 2-09 and Acm-JRL 2 dissociated more slowly from the spike protein than an association was able to be measured, whereby the measured values on the chip increased at a constant rate. The measured values of the different injections of the respective lectin batches are shown in dependence on the time in FIG. 12. The surface containing the bound spike protein was regenerated with 80% ethylene glycol between the individual measurements.

The sensorgram of the SPR analysis of the binding kinetics and the affinity test is shown for SARS-CoV2 spike protein and different lectin batches isolated from bromelain (HZI 2-05, HZI 2-06, HZI 2-09, HZI 2-10, Acm-JRL 2) in increasing concentrations. The $K_D$ values and association constants and $R_{max}$ values were calculated using Biacore X100 software (Table 3). We were able to show that the lectin batches HZI 2-09, HZI 2-10, and Acm-JRL 2 have a high affinity to the SARS-CoV-2 spike protein in the micromolar range. A fast binding ($K_a$ value 1031 1/Ms) and slow dissociation ($K_d$ value 0.003 1/s) of the spike protein could furthermore above all be observed.

TABLE 3

Surface plasmon resonance spectroscopy (SPR binding kinetics and affinity test for SARS-CoV2 spike protein and different lectin batches isolated from bromelain. The values calculated with the Biacore X100 software are shown.

| Lectin | $K_a$ (1/Ms) | $K_d$ (1/s) | $K_D$ (mol/l) | $R_{max}$ (RU) |
|---|---|---|---|---|
| HZI 2- 05 | 132.6 | 0.005 | $4.12 \times 10^{-5}$ | 746.9 |
| HZI 2- 06 | 358.7 | 0.008 | $2.288 \times 10^{-5}$ | 369.3 |
| HZI 2- 09 | 331.0 | 0.003 | $8.249 \times 10^{-6}$ | 627.6 |
| HZI 2- 10 | 285.5 | 0.003 | $9.999 \times 10^{-6}$ | 373.6 |
| Acm-JRL-2 | 1031 | 0.003 | $2.626 \times 10^{-6}$ | 660.0 |

Figure 13:
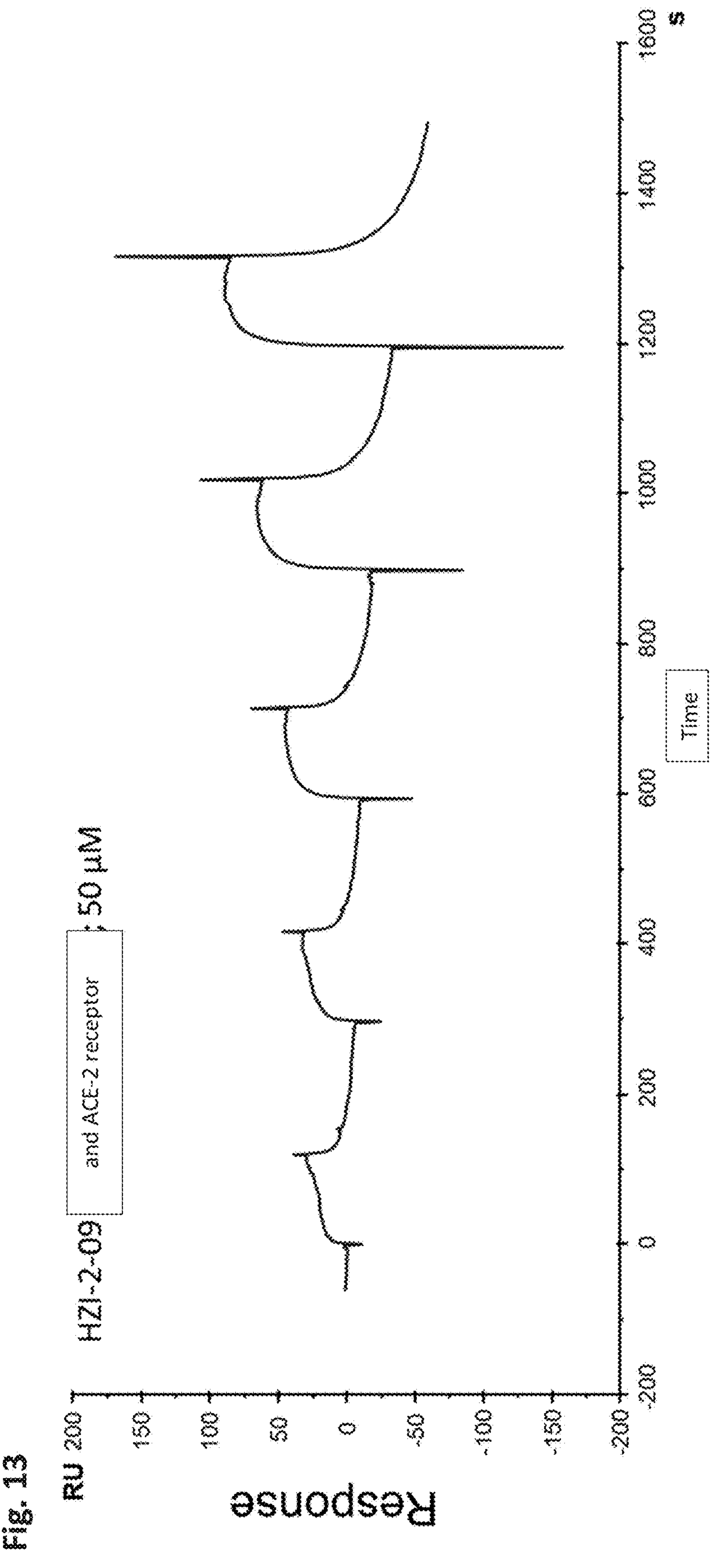
FIG. 13 shows surface plasmon resonance spectroscopy (SPR) binding kinetics and an affinity test for ACE-2 receptor and lectin HZI 2-09. Increasing concentrations of the ligand (highest concentration: 50 μM, starting therefrom 5 1:1 dilutions) were injected for single cycle measurements.

In a further trial, the SPR assay was examined for the analysis of the binding kinetics and the affinity test of the lectin at the ACE-2 receptor (FIG. 13). Lectin concentrations between 3.125 and 50 μM were used for this purpose.

The sensorgram of the SR analysis of the binding kinetics and of the affinity test for the ACE-2 receptor and the lectin batch HTI 2-9 is shown in increasing concentrations in FIG. 13. A conclusion can be drawn from the sensorgram that a dissociation constant of 100 μM or higher is present. In addition, different binding characteristics with respect to the on-off rate are shown. The $K_D$ cannot be calculated using the measurement since it is outside the measured concentrations.

2.2 SARS-CoV-2 Spike SDS-PAGE and LC-MS Analytics

Figure 14:
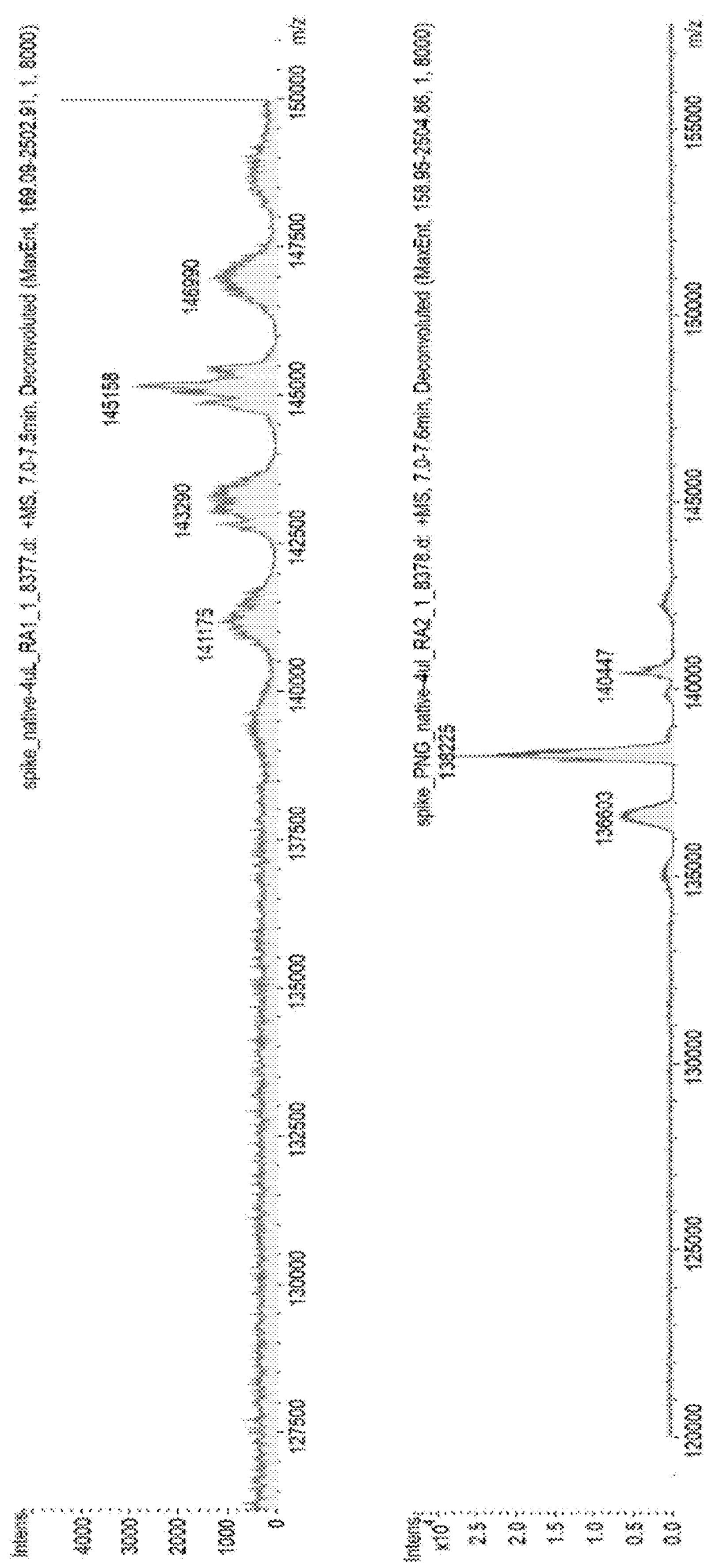
FIG. 14 shows deconvoluted mass spectograms of recombinant SARS-CoV-2 spike (shown at the top) and recombinant SARS-CoV-2 spike digested with PNGase F (shown at the bottom) to detect the glycosylation.

The glycolization of the spike protein was demonstrated by means of LC-MS analytics. The deconvoluted mass spectograms are shown in FIG. 14. PNGase F removes N bound oligosaccharides from glycoproteins. In this respect, splitting takes place between the innermost GIC-NAc and asparagine residues of oligosaccharides. After the digestion of the recombinant SARS-CoV-2 spike protein using PNGase F, a mass shift in the mass spectrograph can be recognized, triggered by the loss of oligosaccharides from the spike protein.

Figure 16:
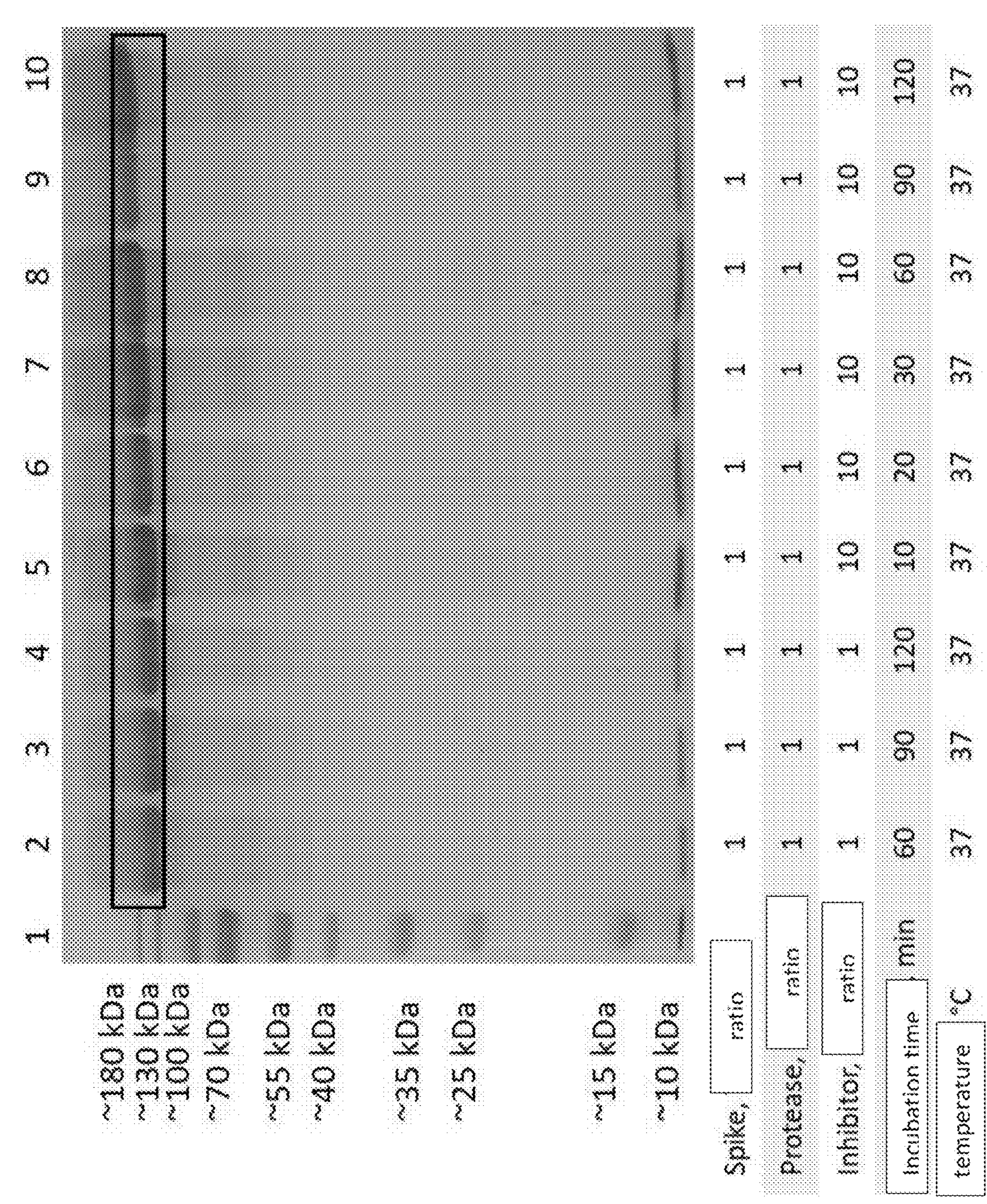
FIG. 16 shows an SDS-PAGE for detecting the proteolytic degradation of the recombinant SARS-CoV-2 spike and of the inhibiting function of HZI 2-07 for the bromelain protease fraction HZI 2-08. SARS-CoV-2 spike with bromelain protease function HZI 2-08 and bromelain inhibitor HZI 2-07 in the quantity of material ratio 1:1:1 and 1:1:10 1) PageRulerPrestained. The rectangle marks the intact spike protein at approximately 150 kDA.
Figure 17:
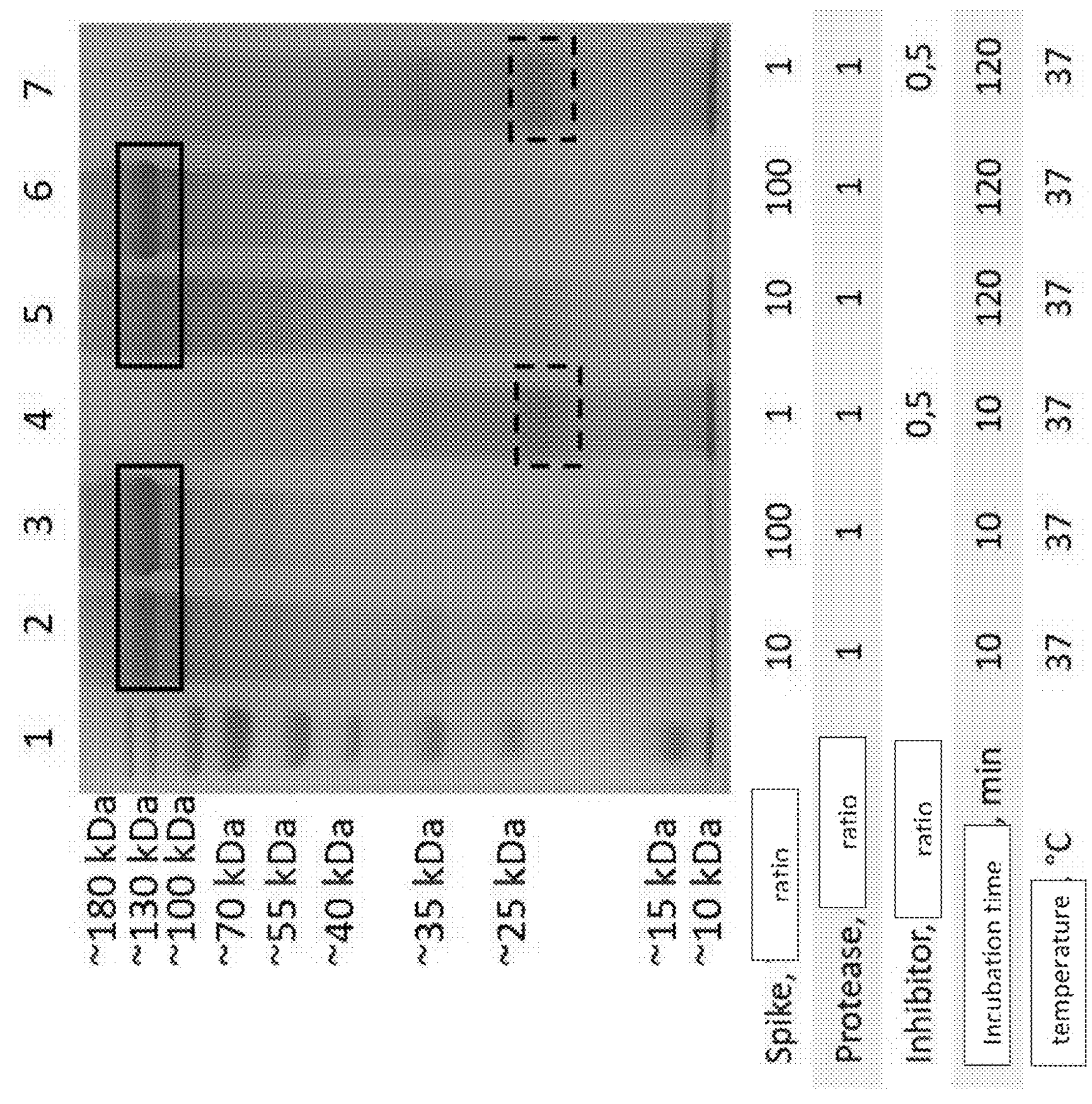
FIG. 17 shows an SDS-PAGE for detecting the proteolytic degradation of the recombinant SARS-CoV-2 spike and of the inhibiting function of HZI 2-07 for the bromelain protease fraction HZI 2-08. SARS-CoV-2 spike with bromelain protease (HZI 2-08) in the quantity of material ratio 10:1 and 100:1 and SARS-CoV-2 spike with bromelain protease HZI 2-08 and bromelain inhibitor HZI 2-07 in the quantity of material ratio 1:1:0.5. 1) PageRulerPrestained. The rectangle marks the intact spike protein at approximately 150 kDa; the dashed rectangle shows the spike degradation product at approximately 24 kDa.
Figure 19:
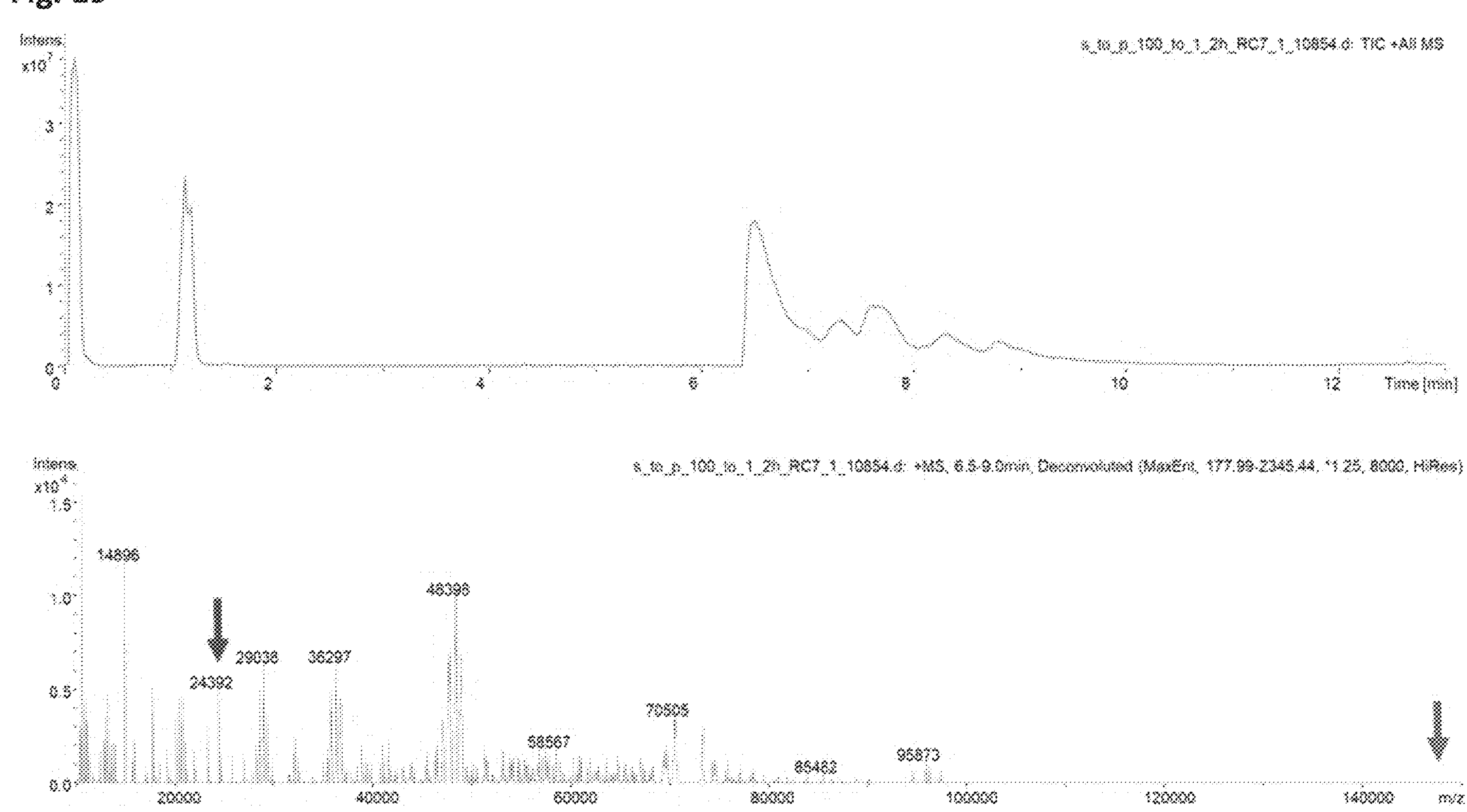
FIG. 19 shows a total ion chromatograph and a deconvoluted mass spectrograph of recombinant SARS-CoV-2 spike incubated with bromelain protease fraction HZI-2-08 in the quantity of material ratio 100:1, 2 h, 37° C. The right arrow marks the intact spike protein at approximately 150 kDA; the left arrow shows the spike degradation product of 24 kDa.
Figure 20:
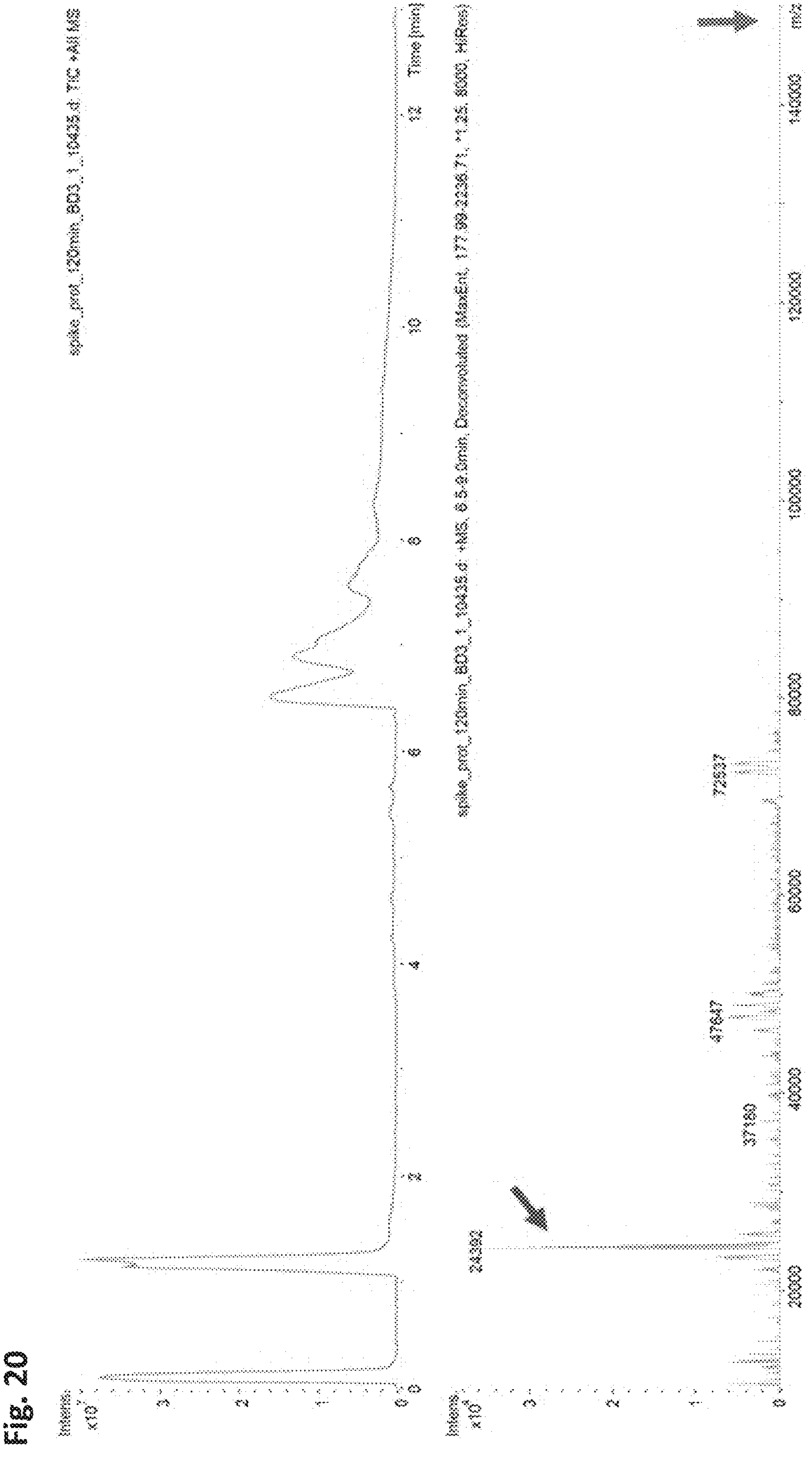
FIG. 20 shows a total ion chromatograph and a deconvoluted mass spectrograph of recombinant SARS-CoV-2 spike incubated with bromelain protease fraction HZI-2-08 in the quantity of material ratio 1:1, 2 h, 37° C. The right arrow marks the intact spike protein at approximately 150 kDA; the left arrow shows the spike degradation product of 24 kDa.

SDS-PAGE and fluid chromatography coupled with mass spectrometry was used for the analytical demonstration of the proteolysis activity of the bromelain protease fraction HZI 2-08 and of the inhibitory function of the peptide HZI 2-07 acquired from bromelain. The fragmentation of the recombinant SARS-CoV2 spike and the inhibitory function of HZI 2-07 were able to be demonstrated via SDS-PAGE (FIGS. 15-17). The mass spectra and the neutral masses deconvoluted therefrom can likewise demonstrate the fragmentation (FIGS. 18-21).

The proteolytic degradation of the SARS-CoV-2 spike protein by the protease (HTI 2-08) can be recognized in lanes 2 to 7 in FIG. 15. The main mass of approximately 150 kDa of the intact spike cannot be demonstrated. However, a main degradation product can be recognized at approximately 24 kDa (dashed rectangle in FIG. 15). After the addition of HZI 2-07 (=inhibitor), the inhibitory function becomes visible—a degradation of the spike protein is inhibited. This results in bands at approximately 150 kDa in lanes 8-10 (rectangle in FIG. 15).

The inhibitory action of the inhibitor on the protease (HZI 2-08) is maintained over a longer trial time period; testing took place up to 120 min. This can be recognized at the intact spike protein in FIG. 16 that was marked by a rectangle.

The kinetics of the proteolytic degradation of the spike protein is show in FIG. 17. At a spike:protein ratio of 10:1, a significant band at approximately 150 kDa (row 2) can be recognized after a 10 minute incubation, which indicates an intact spike protein. After a longer incubation of 120 min (lane 5), it can be recognized that the band has already substantially disappeared, the fragmentation increases. This is not the case at a ratio of 100:1 (lanes 3 and 6). The intact protein can also be seen here after a 120-minute incubation, which indicates an insufficient action of the protease HZI 2-08. An optimum ratio of spike:protease of 1:1 thus results with the results that are shown in FIG. 15 and FIG. 16. It can furthermore be concluded that the ratio of 1:1:0.5 (spike: protease:inhibitor) is unfavorable since the degradation of the spike was unable to be inhibited. The ratio 1:1:1 appears optimum here (FIG. 16).

The total ion chromatograph (TIC) and the mass spectrum of the SARS-CoV-2 spike protein are shown in FIG. 18. After addition of the protease (HZI 2-08; ratio spike:protease: 100:1) no mass peak could be demonstrated at 150 kDa after 10 min (arrow). The fragments that occur indicate an effective degradation of the spike protein after a protease addition. This confirms the results that were already represented by means of SDS-PAGE (FIG. 15).

No mass peak could also be demonstrated at 150 kDa (right arrow, FIG. 19) after a 120 min. incubation with the protease (HZI 2-08; ratio spike:protease:100:1). This indicates that the proteolytic action of the protease remains constant over a time period of at least 120 min. In addition, a mass peak is now visible at m/z 24.392, which represents the main degradation product of the spike protein. This confirms the results that were already represented by means of SDS-PAGE (FIG. 15).

The proteolytic action of the protease (HZI 2-08) again becomes clear in FIG. 17). A spike with a protease is here present in a ratio of 1:1: The peak of the degradation product (left arrow) is very pronounced after 120 min incubation.

Figure 21:
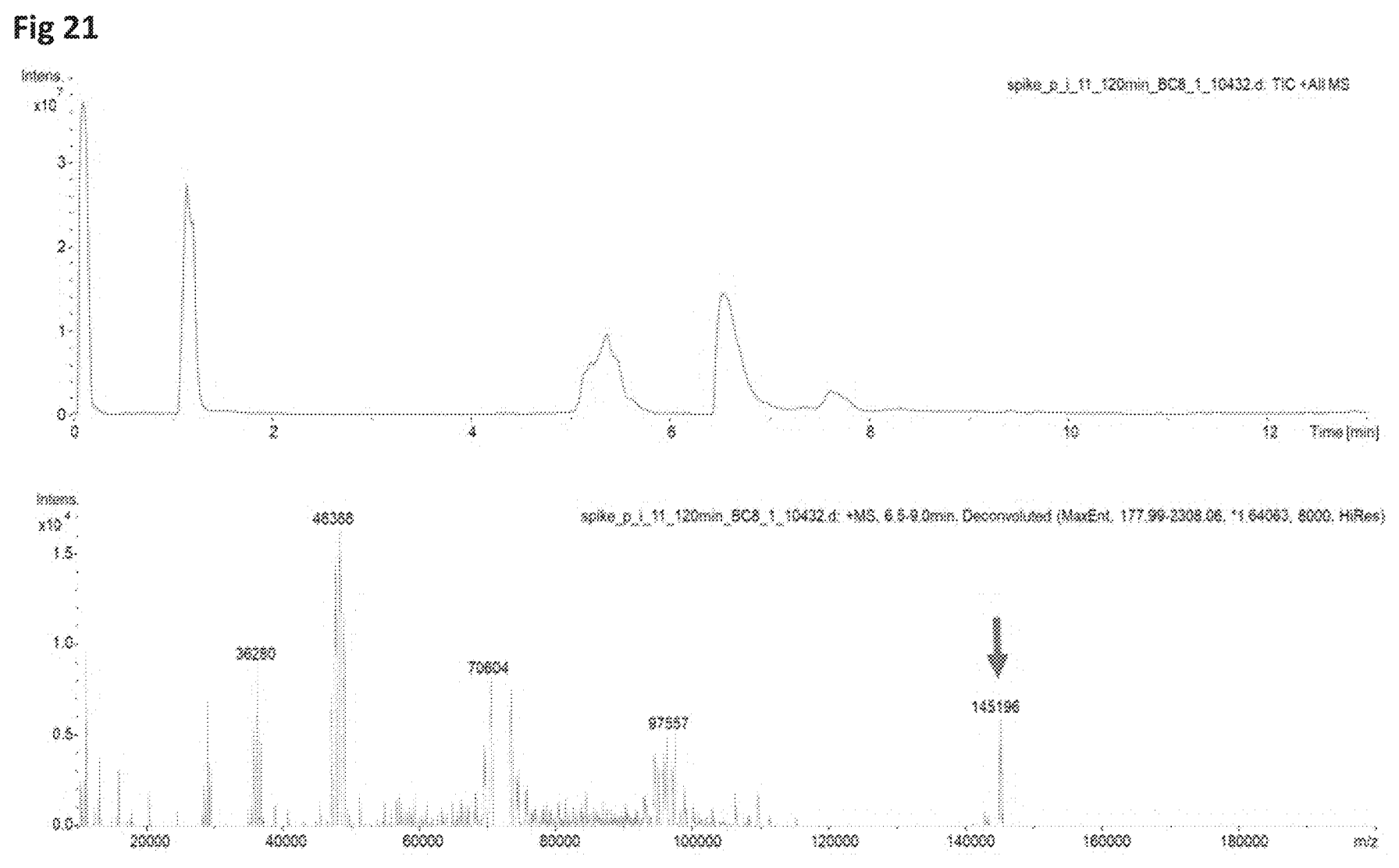

After addition of the inhibitor HZI 2-07, the intact spike protein becomes visible at m/z 145.196 (FIG. 21). The degradation product at 24 kDA cannot be detected. This confirms the result of FIG. 15 where it has already been able to be shown that the inhibitor inhibits the protease (HZI 2-08). The spike protein can accordingly not be degraded.

Figure 22:
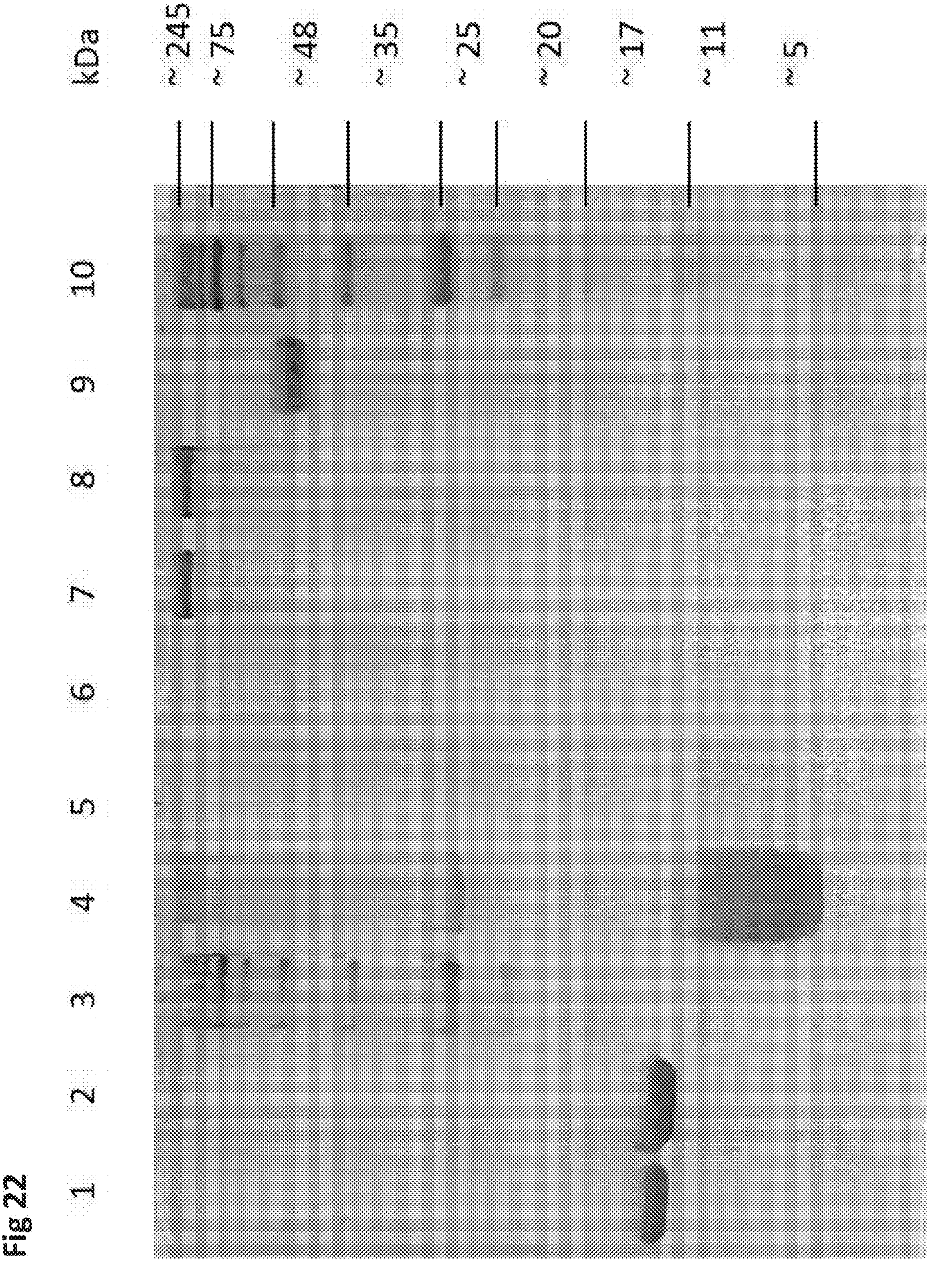
FIG. 22 shows an SDS PAGE gel in which recombinant SARS-CoV-2 spike protein incubated with bromelain (raw fraction) was applied; SARS-CoV-2 spike protein not bromelain incubated is also shown for comparison. Details of SDS-PAGE analysis: Lane 1: 2 μg lectin batch HZI 2-09. Lane 2: 2 μg lectin batch HZI 2-10. Lane 4: 40 μg bromelain (Ursapharm). Lanes 5-6: 1 μg recombinant SARS-CoV-2 spike and 0.4 μg bromelain after 1 h incubation at 37° C. (quantity of material ratio protein:protease~1:1). Lanes 7/8: 1/1.5 μg recombinant SARS-CoV-2 spike. Lane 9: 2 μg horseradish peroxidase Lanes 3/10: 3.5 μl SERVA Triple Color Protein Standard III. (T=14%, C=5%; samples were reduced before application with DTT and were heat denatured and centrifuged while adding SDS at 95° C. for 3 min.).

FIG. 22 shows an SDS-PAGE analysis of recombinant SARS-CoV-2 spike protein after 1 h digestion with bromelain base powder at 37° C. (material quantity ratio protein: protease approximately 1:1, lanes 5 and 6). SARS-CoV-2 spike protein not incubated with bromelain is also shown for comparison. (lanes 7 and 8). The results show that bromelain base powder is also able to digest the spike protein.

It was thus able to be shown that bromelain can bind to the spike protein of coronaviruses and that the lectin contained in bromelain (5% of the total bromelain) can bind both to the spike protein and to mannose, but not to the ACE-2 receptor of the host with a comparable $K_D$.

The invention claimed is:

1. A method of treating a human or animal infected by a coronavirus, or providing prophylaxis against a coronavirus infection, wherein the coronavirus is selected from the group consisting of severe acute respiratory syndrome coronavirus 2 (SARS-CoV-2) and synonymous or non-synonymous mutants thereof and variants thereof and those selected from the group consisting of B.1.1.7, B.1.351, B.1.617, P.1, B.1.525, P.2, B.1.427, B.1.429, L452R, Fin-796H, B.1.526, S:H66D, S:G142V, S:D215G, S:V483A, S:D614G, S:H655Y, S:G669S, S:Q949R, S:N1187D, ORF6:K23–, ORF6:V24–, ORF6:S25–, ORF6:I26–, ORF6:W27–, ORF6:N28–, ORF6:L29–, ORF6:D30–, ORF6:Y31–, S:Y144–, E484K, VOC 20I/484Q, B.1, R.1, A.2.5, C.36, B.1.1.318, B.1.621, and B.1.623, the method comprising administering to the human or animal an effective amount of a combination preparation containing at least one bromelain protease and at least one jacalin-related lectin, wherein the at least one bromelain protease is selected from the group consisting of stem bromelain (SBM) (EC 3.4.22.32), fruit bromelain (EC 3.4.22.33), and ananain (EC 3.4.22.31), and wherein the jacalin-related lectin is pineapple lectin or jacalin-related lectin from *Ananas comosus* (AcmJRL), and wherein the weight ratio of the totality of the bromelain protease to the totality of the jacalin-related lectin is 50:50 to 0.1:99.9.

2. The method according to claim 1, wherein the total concentration of all the bromelain proteases in the combination preparation amounts to 0.01 to 50.0 wt % and/or the total concentration of all the jacalin-related lectin in the extract amounts to 0.01 to 60.0 wt %.

3. The method of claim 1, wherein a symptom caused by an infection includes fever, coughing, pneumonia, lymphopenic community acquired pneumonia (L-CAP), pleuritis, shortage of breath, indisposition and/or fatigue, sputum, anosmia, ageusia, shortness of breath, muscular inflammation and/or inflammations of the throat, joint pain, chest pain, sore throat, headache, backache, ague, nausea, vomiting, colds, diarrhea, coughing blood, lymphopenia, skin rash on hands, feet, or in the mouth, nonsuppurative conjunctivitis at both sides, hypotonia, shock, hypercytokinemia, dysfunction of the cardiac muscle, inflammation of the pericardium and/or of the cardiac valve, blood coagulation dysfunctions, multisystem inflammatory syndromes in children (MIS-c), or welling of the conjunctiva, or a combination thereof.

4. The method of claim 1, wherein the at least one bromelain protease is included in an amount of 0.1 to 80.0 wt. % or the at least one jacalin-related lectin is included in an extract in an amount of 0.01 to 50.0 wt. %.

5. The method of claim 1, wherein the combination preparation is in the form of or as a component of a powder, a granulate, a tablet, a hard capsule, a soft capsule, an effervescent tablet, a solution, an emulsion, a suspension, a salve, a cream, a paste, a gel, a tincture, eye drops, an inhalation powder, a nose spray, a suppository, or a transdermal patch.

6. The method of claim 1, wherein the combination preparation is administered orally, intravenously, subcutaneously, or intramuscularly, by infusion onto the mucous membranes of the nose, of the mouth or of the pharynx, by inhalation, by application onto the surface of the eyes, rectally and/or by a transdermal patch.

7. The method of claim 1, wherein the administration takes place from once a week up to once an hour.

* * * * *